(12) United States Patent
Straub et al.

(10) Patent No.: US 11,911,103 B2
(45) Date of Patent: Feb. 27, 2024

(54) PERSONALIZED PATIENT INTERFACE FOR OPHTHALMIC DEVICES

(71) Applicant: Carl Zeiss Meditec, Inc., Dublin, CA (US)

(72) Inventors: Jochen Straub, Pleasanton, CA (US); Kabir M. Arianta, Livermore, CA (US); Mahsa Darvishzadeh Varcheie, Fremont, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 459 days.

(21) Appl. No.: 17/122,147

(22) Filed: Dec. 15, 2020

(65) Prior Publication Data

US 2021/0186319 A1    Jun. 24, 2021

Related U.S. Application Data

(60) Provisional application No. 62/949,693, filed on Dec. 18, 2019.

(51) Int. Cl.
*A61B 3/00* (2006.01)
*A61B 3/024* (2006.01)
*A61B 3/10* (2006.01)
*A61B 3/12* (2006.01)
*A61B 3/16* (2006.01)
(Continued)

(52) U.S. Cl.
CPC .......... *A61B 3/0083* (2013.01); *A61B 3/0091* (2013.01); *A61B 3/024* (2013.01); *A61B 3/102* (2013.01); *A61B 3/1015* (2013.01); *A61B 3/12* (2013.01); *A61B 3/1241* (2013.01); *A61B 3/16* (2013.01); *A61F 9/009* (2013.01); *A61F 9/0026* (2013.01); *A61F 9/045* (2013.01)

(58) Field of Classification Search
CPC ..... A61B 3/0083; A61B 3/0091; A61B 3/024; A61B 3/1015; A61B 3/102; A61B 3/12; A61B 3/1241; A61B 3/16; A61F 9/0026; A61F 9/009; A61F 9/0045
USPC ......................................................... 351/205
See application file for complete search history.

(56) References Cited

U.S. PATENT DOCUMENTS

| 5,912,723 A | 6/1999 | Maddess |
| D472,637 S | 4/2003 | Cooper et al. |

(Continued)

FOREIGN PATENT DOCUMENTS

| JP | 2017035739 A | * | 2/2017 |
| WO | WO-2012059236 A1 | | 5/2012 |

(Continued)

OTHER PUBLICATIONS

JPO 2017-035739 English translation.*

(Continued)

*Primary Examiner* — William R Alexander
*Assistant Examiner* — Sharrief I Broome
(74) *Attorney, Agent, or Firm* — Snell & Wilmer L.L.P.

(57) ABSTRACT

A medical ophthalmic system uses a patient-specific face mask to establish a predefined alignment between the ophthalmic system and an eye of a patient. The patient-specific face mask may optionally provide a light proof enclosure for the eye. The face mask may be coupled directly to an ophthalmic device, or its housing/enclosure, of the ophthalmic system. The face mask may be 3D printed based on a 3D model of the patient's face.

29 Claims, 13 Drawing Sheets

(51) Int. Cl.
*A61F 9/00* (2006.01)
*A61F 9/009* (2006.01)
*A61F 9/04* (2006.01)

(56) References Cited

U.S. PATENT DOCUMENTS

| | | |
|---|---|---|
| 6,549,801 B1 | 4/2003 | Chen et al. |
| 6,741,359 B2 | 5/2004 | Wei et al. |
| 7,301,644 B2 | 11/2007 | Knighton et al. |
| 7,827,038 B2 | 11/2010 | Richard et al. |
| 8,132,916 B2 | 3/2012 | Johansson |
| 8,371,696 B2 | 2/2013 | Johansson |
| 8,668,338 B2 | 3/2014 | Johansson et al. |
| 8,931,905 B2 | 1/2015 | Waller et al. |
| 8,967,806 B2 | 3/2015 | Bublitz et al. |
| 8,998,411 B2 | 4/2015 | Tumlinson et al. |
| 9,332,902 B2 | 5/2016 | Tumlinson et al. |
| 9,456,746 B2 | 10/2016 | Bublitz et al. |
| 9,700,206 B2 | 7/2017 | An et al. |
| 9,706,915 B2 | 7/2017 | Everett et al. |
| 9,759,544 B2 | 9/2017 | An et al. |
| 9,772,497 B1 | 9/2017 | Hewlett et al. |
| 2005/0171438 A1 | 8/2005 | Chen et al. |
| 2010/0027857 A1 | 2/2010 | Wang |
| 2012/0277579 A1 | 11/2012 | Sharma et al. |
| 2012/0305003 A1 | 12/2012 | Mark |
| 2012/0307014 A1 | 12/2012 | Wang |
| 2013/0339043 A1* | 12/2013 | Bakar ............. G16H 20/10 705/2 |
| 2014/0261430 A1 | 9/2014 | Davis |
| 2014/0267668 A1 | 9/2014 | Ignatovich et al. |
| 2015/0070650 A1* | 3/2015 | Seriani ............. G02C 13/005 351/204 |
| 2015/0131050 A1 | 5/2015 | Bublitz et al. |
| 2016/0262617 A1* | 9/2016 | Gerrans ............. A61B 3/0083 |
| 2019/0160247 A1* | 5/2019 | Kimmel ............. A61M 16/0605 |
| 2019/0254518 A1* | 8/2019 | Rafaeli ............. A61B 3/14 |
| 2019/0274545 A1 | 9/2019 | Pascal et al. |

FOREIGN PATENT DOCUMENTS

| | | | |
|---|---|---|---|
| WO | WO-2016124644 A1 | 8/2016 | |
| WO | WO-2016145021 A1 * | 9/2016 | ......... A61B 3/0058 |
| WO | WO-2017048873 A1 * | 3/2017 | ......... A61B 3/0083 |
| WO | WO-2019092697 A1 | 5/2019 | |

OTHER PUBLICATIONS

Blazkiewicz et al., (2005). "Signal-To-Noise Ratio Study of Full-Field Fourier-Domain Optical Coherence Tomography," Applied Optics, 44(36):7722-7729.

Carl Zeiss Meditec Inc., (2005). "GDxVCC User Manual, Revision Control," PN 58655-1 Rev A, Software Ver. 5.5.0, 130 pages.

Carman, (2019). "Neutrogena will 3D print custom face masks based on buyer's skin measurements", available online at <www.theverge.com/2019/1/3/18165651/neutrogena-maskid-app-cutoms-face-mask-ces-2019>, 3 pages.

Hillmann et al., (2011). "Holoscopy—Holographic Optical Coherence Tomography," Optics Letters, 36(13):2390-2.

International Search Report and Written Opinion received for International Patent Application No. PCT/EP2020/086169 dated Mar. 18, 2021, 11 pages.

Nakamura et al., (2007). "High-Speed Three Dimensional Human Retinal Imaging by Line Field Spectral Domain Optical Coherence Tomography," Optics Express, 15(12):7103-7116.

* cited by examiner

PERSONALIZED PATIENT INTERFACE FOR OPHTHALMIC DEVICES

PRIORITY

This application claims priority to U.S. Provisional Application Ser. No. 62/949,693 filed Dec. 18, 2019, the contents of which are hereby incorporated by reference.

FIELD OF INVENTION

The present invention is generally directed to ophthalmic systems. More specifically, it is directed to a system, device, and/or method for aligning an ophthalmic device to a patient's eye. In particular, it is directed to ophthalmic systems that support self-administered ophthalmic procedures (e.g., self-administered ophthalmic examination, self-administered ophthalmic medication, self-administered ophthalmic diagnostics, self-administered ophthalmic testing, self-administered ophthalmic imaging, self-administered ophthalmic treatment, etc.)

BACKGROUND

Ophthalmic systems/devices need to be aligned relative to a patient's eye, and particularly may require alignment a patient's pupil. Although different ophthalmic systems have different levels of alignment requirements, all require some level of alignment, and some have very high alignment requirements for proper operation. Some ophthalmic systems place alignment requirements on the pupil of a patient's eye with sub-millimeter accuracy in three spatial dimensions. Typically, the higher the alignment requirements, the more complicated/involved the system procedures to achieve precise alignment. In such cases, the alignment task is traditionally performed by an ophthalmic technician or by an automated positioning system.

System-to-patient alignment can be difficult to achieve, particularly when it is desirable for the system to support self-administered ophthalmic procedures, such as for at-home, portable, and/or personal use. Such systems cannot rely on an operator to provide the system-to-patient alignment. Furthermore, such systems often have low-cost requirements, which can severely limit the use of automated alignment sub-systems since they typically tend to be complex, expensive, and prone to reliability problems.

Various different types of ophthalmic systems/devices are known, and they are often used for diagnostic and/or therapeutic (e.g., treatment) purposes. Example of ophthalmic therapeutic systems/devices may be an ophthalmic medication delivery system (manual, automated, or semi-automated systems) or an ophthalmic treatment system such as a system used in an ophthalmic medical procedure, e.g., ophthalmic laser surgery. Examples of ophthalmic diagnostic systems/devices may include visual field test perimeters, autorefractors, corneal pachymeters, ophthalmic ultrasound devices, slit lamps, tonometers, surgical apparatuses/tools, and various ophthalmic imaging systems. Ophthalmic devices, in general, require some alignment of the device to a patient's eye, with some devices having more critical alignment requirements than others. Herein is presented an alignment system/method suitable for ophthalmic systems, in general, but also capable of repeatably and consistently providing high levels of eye alignment for more critical applications.

Although the present invention is not limited to any specific type of ophthalmic system (diagnostic and/or therapeutic), for the sake of brevity, the present discussion relates to ophthalmic imaging systems as exemplary systems using the present invention with the understanding that the present invention may be applied to other types of ophthalmic systems, such as visual field test perimeters, etc.

One example of an ophthalmic imaging system is a fundus imager, which is typically used to image the fundus (or retina) of an eye. The fundus is the interior surface of the eye opposite the eye lens (or crystalline lens) and may include the retina, optic disc, macula, fovea, and posterior pole. Two categories of fundus imagers used to image the fundus are flood illumination imagers and scan imagers. Scan imagers may further be divided into confocal point scanning fundus imagers and line scanning imagers. Another example of an ophthalmic imaging device is an optical coherence tomography (OCT) system, which permits in situ real-time cross-sectional (e.g., depth) imaging of tissue, e.g., imaging of the anterior or posterior of an eye. OCT systems measure the scattering profile of an OCT beam as it impacts a sample (e.g. the eye fundus), and can construct one-dimensional (1D) depth information at a single point, two-dimensional (2D) cross-sectional images and en face images, and three-dimensional (3D) volume images. Multiple OCT images may be taken at the same location, and processed to extract motion information, such fluid (e.g., blood) flow. OCT systems that extract blood flow information may be termed OCT Angiography (OCTA) systems.

Irrespective of the type of ophthalmic system, correct alignment of the human eye to the ophthalmic diagnostic system can be critical to performance. For example, correctly aligning the pupil of the eye to the exit pupil (or aperture) of an ophthalmic imaging system is critical for imaging the human retina with fundus cameras or OCT systems. In Fundus Imagers, this is complicated by the need to divide an imaging system's aperture into an illumination pupil through which light enters the eye and a collection pupil through which light exiting the eye is collected for imaging (e.g., for collecting image data). Typical ophthalmic imaging systems are usually operated by a technician who uses various feedback mechanisms and alignment aides to position the ophthalmic imaging system, which is typically mounted on an adjustable mechanical stage, relative to a patient whose head is held in a fixed position by a rigid chinrest. Automatic control systems that use various feedback mechanisms for alignment have been demonstrated, but such automated systems increase system complexity, cost, and tend to require regular maintenance for optimal performance.

Smaller, lower cost, portable or handheld ophthalmic imaging systems have been proposed. But such systems still require a trained technician, and typically also require the use of eyecups, stabilizing bars, and the like, to attempt to achieve repeatable positioning of the imaging systems to the patient's eye. Further complicating their use, lower cost portable systems tend to have a reduced set of alignment aids for the technician and therefore require a higher degree of skill to achieve good image data.

A large fraction of the cost of ophthalmic imaging systems devices goes towards the achievement of device-to-patient alignment both in terms of mechanical placement of the imaging device relative to the eye, and alignment aides which help the operator and/or automated system know how to move the device to achieve best alignment.

Another alignment approach may be termed "self-alignment," which may be used as part of a self-administered ophthalmic procedure. In this approach, a patient moves himself/herself and/or the imaging device to achieve alignment between the two. Generally, to facilitate self-alignment, it is desirable that the imaging system have alignment aids to provide the patient with feedback to make the correct alignment modifications with minimal effort and training, and acquire a good measurement with high repeatability. Such systems require collaboration (e.g., willing cooperation) from the patient, including but not limited to physical movement and mental processing of feedback. A situation where this approach is desirable is for personal and/or at-home care.

Home care and/or assisted living care is set to become an increasingly important market as the need for at-home solutions increases, particularly as the cost of various components of ophthalmic diagnostic systems (e.g., digital cameras and computing equipment) goes down. Home care presents a special case in which an auxiliary operator (e.g., technician) is less likely to be available to help acquire the image data. In this case, the patient and ophthalmic diagnostic system must work together to acquire good data without dramatically increasing cost or decreasing ease-of-use.

To aid alignment, ophthalmic imaging systems generally provide several forms of visual stimuli to the eye of a person whose retina is being imaged. Good alignment may require that: 1) the pupil of the eye be positioned accurately in three dimensions relative to the system's illumination pupil (aperture) and collection pupil (aperture); 2) the gaze of the eye is in the correct angular direction; and 3) the retina is in focus. Generally, imaging systems provide alignment aids (e.g., feedback mechanisms) for only the illumination pupil of the system, and do not provide alignment information relating to the system's collection pupil.

To assist a technician achieve proper alignment, the imaging system may provide a secondary illumination and imaging system to provide a preview of the patient's retina prior to actuating the capture of image data. The secondary illumination system may be a low intensity white light, low intensity red light to which the human eye has relatively low sensitivity, or an infrared light to which the eye has very low sensitivity. When a device is properly aligned, this light may cover a region of the retina slightly wider than the field of view of the imaging system. When a subject approaches the aperture of the system from a distance, the subject can visualize the illumination pupil of the camera as an illuminated virtual object, a few millimeters in diameter, apparently floating in space a few centimeters beyond the objective lens of the imaging system. As the subject comes closer to correct alignment, looking into the fundus camera and moving his eye towards superimposition with the illuminated virtual object, it becomes impossible to focus on that virtual object, and the subject may begin to see the shadow of his own eye pupil, as illuminated by the virtual object near the eye. This may appear to the subject as a circularly illuminated field which increases in size as the subject approaches the correct axial location, and shifts in lateral position depending on the lateral alignment. When the subject successfully places the eye such that the illumination reaches a maximum field size and maximum brightness, the pupil of the eye may be assumed to be aligned with respect to the illumination pupil of the imaging system and most of the light is passing through uninhibited.

Fixation targets are commonly used to orient the gaze direction of a subject to a particular direction. Frequently, the fixation target is presented through the optics of the ophthalmic imaging system to the same eye being imaged. The fixation target may be moved relative to the field of view of the ophthalmic imaging system in order to guide the subject such that different portions of the retina are within the system's field of view. Multiple images acquired with different fixation locations may be montaged together to form a mosaic image spanning a larger field of view than what could be collect in a single exposure. Such fixation targets are commonly presented such that they are in focus for the subject, and have at least some feature with small angular extent such that the subject may orient gaze direction with high precision. Some fixation targets may include a region of larger lateral extent, especially for individuals with low central vision, who may not be able to perceive a small target at the center of field. The subject may have access to a focus knob and control the position of lenses inside the system such that fixation focus is optimized. Optionally, the fixation target may be projected back through the collection pupil. In this case, seeing the fixation target is enough to verify that at least some portion of the collection pupil is unobstructed.

As is evident from the above, achieving proper alignment of a patient's eye to an ophthalmic system is a complicated, but critical task. In summary, ophthalmic systems generally need to be aligned relative to the pupil of the patient's eye with sub-millimeter accuracy in three dimensions. This task has traditionally been performed by a trained ophthalmic technician, and/or may be facilitated by use of an automated positioning system. Both of these approaches introduce complexity and cost constraints, and neither lend themselves easily to self-administered ophthalmic procedures, such as for at-home use (home care). A patient at home cannot rely on an operator (e.g., visiting technician) to provide machine alignment, and automated systems are complex, expensive, and prone to reliability problems, which a patient cannot be expected to address. Previous self-alignment approaches still tend to be complicated, unreliable, and often difficult for the elderly and incapacitated to achieve.

It is an object of the present invention to reduce the complexity of aligning a patient's eye to an ophthalmic system.

It is another object of the present invention to provide an ophthalmic patient-to-device alignment system suitable for self-administered procedures, self-alignment, and/or home-care uses.

It is a further object of the present invention to provide an ophthalmic system that provides repeatable, high accuracy alignment with minimal technician training.

It is still another object of the present invention to reduce the cost of ophthalmic patient alignment systems, particularly for home use.

It is another object of the present invention to facilitate the self-administering of ophthalmic procedures, including imaging, treatment, medicating and diagnostic related procedures.

SUMMARY OF INVENTION

The above objects are met in a system/device/method that uses a patient-specific, face mask to establish a predefined (known) alignment between an ophthalmic system and a patient's eye. The face mask may be coupled directly to an ophthalmic device (housing/enclosure) of the ophthalmic system or to a base of the ophthalmic system. The face mask may be 3D printed based on a 3D model of the patient's face.

Essentially, all mechanical alignment adjustments of a typical ophthalmic system may be eliminated, including self-alignment adjustments, alignment adjustments operable by a system operator, and automated system adjustments. This is achieved by placing a patient's face in a repeatable position using a personalized face interface consisting of, or including, a full-face or partial-face mask. The face mask may include a molded forehead, nasal bridge, brow bridge, temple, cheek, jaw, chin, or any combination of these.

A 3D scanning application, or software tool, may be used to acquire a 3D model of the patient's face, which may then be used to 3D print the customized face mask, or parts thereof. The 3D model may be acquired by use of a 3D imaging device, such as a multi-camera imaging system or a depth-sensing camera, either of which may be integrated into a hand-held computing device, such as a smart phone or tablet computer. It is to be understood that the 3D model may be acquired by use of any other known 3D scanning/imaging technology, singularly or in combination. Examples of suitable 3D scanning/imaging technologies include laser triangulation 3D scanning technology, structured light 3D scanning technology, contact-based 3D scanning technology, time-of-flight 3D scanning technology, and photogrammetry.

Other objects and attainments together with a fuller understanding of the invention will become apparent and appreciated by referring to the following description and claims taken in conjunction with the accompanying drawings.

Several publications may be cited or referred to herein to facilitate the understanding of the present invention. All publications cited or referred to herein, are hereby incorporated herein in their entirety by reference.

The embodiments disclosed herein are only examples, and the scope of this disclosure is not limited to them. Any embodiment feature mentioned in one claim category, e.g. system, can be claimed in another claim category, e.g. method, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts.

DESCRIPTION OF THE PREFERRED EMBODIMENTS

Ophthalmic systems (e.g. ophthalmic diagnostic systems, ophthalmic therapeutic systems (e.g. ophthalmic lasers, such as yttrium aluminum garnet, YAG, lasers), and ophthalmic medicating, or medication dispensing, systems) generally have some level of patient-to-instrument alignment requirements to achieve a proper operation. Systems that have higher alignment requirements are generally limited to a clinical setting where a system operator (e.g., technician) may assist with the system's alignment process. Ophthalmic systems that support self-administered ophthalmic procedures (such as at-home, "self-acquisition," and/or "self-testing") ophthalmic devices generally rely on the patient to self-align his/her eye to the ophthalmic system. Small or portable ophthalmic systems, such as the ZEISS Matrix® desktop perimeter (a frequency doubling technology (FDT) perimetry device), may be designed with a large exit pupil (eye box) to allow for a much wider range of pupil positions and thereby relax its eye-alignment requirements, but such a technique for relaxing alignment requirements is generally not possible in precision ophthalmic systems, such as ophthalmic surgical systems and ophthalmic imaging systems. Ophthalmic imaging systems, such as fundus imagers, optical coherence tomography (OCT) systems, OCT angiography (OCTA) systems, etc., tend to have high eye-to-system alignment requirements. This has hindered their use in self-administered applications (e.g., at-home applications), and generally limited their use to clinical settings requiring a high level of system operator training or automation. The present invention seeks to facilitate the operation of ophthalmic systems, including high precision ophthalmic systems, by providing a mechanism/system to more easily achieved proper patient-to-system alignment.

For exemplary purposes, and to showcase the effectiveness of the present invention, some embodiments of the present invention are herein presented as implemented within an ophthalmic imaging device, but it is to be understood that the present invention may be incorporated into other types of ophthalmic systems, including treatment and medicating systems. Detailed descriptions of some exemplary ophthalmic systems suitable for use with the present invention are provided below, but application of the present invention is not limited to these specific examples and may be applied to any ophthalmic system requiring eye alignment. Examples of ophthalmic systems that may integrate the present invention include a tonometer, an eye medication dispenser/applicator (e.g., eye dropper), a biometry system, a refractor, a visual field tester, a wavefront sensor, a slit lamp, an ophthalmic laser treatment system, a surgical device, a fundus imaging system, an OCT system, and an OCT angiography system.

Figure 1:
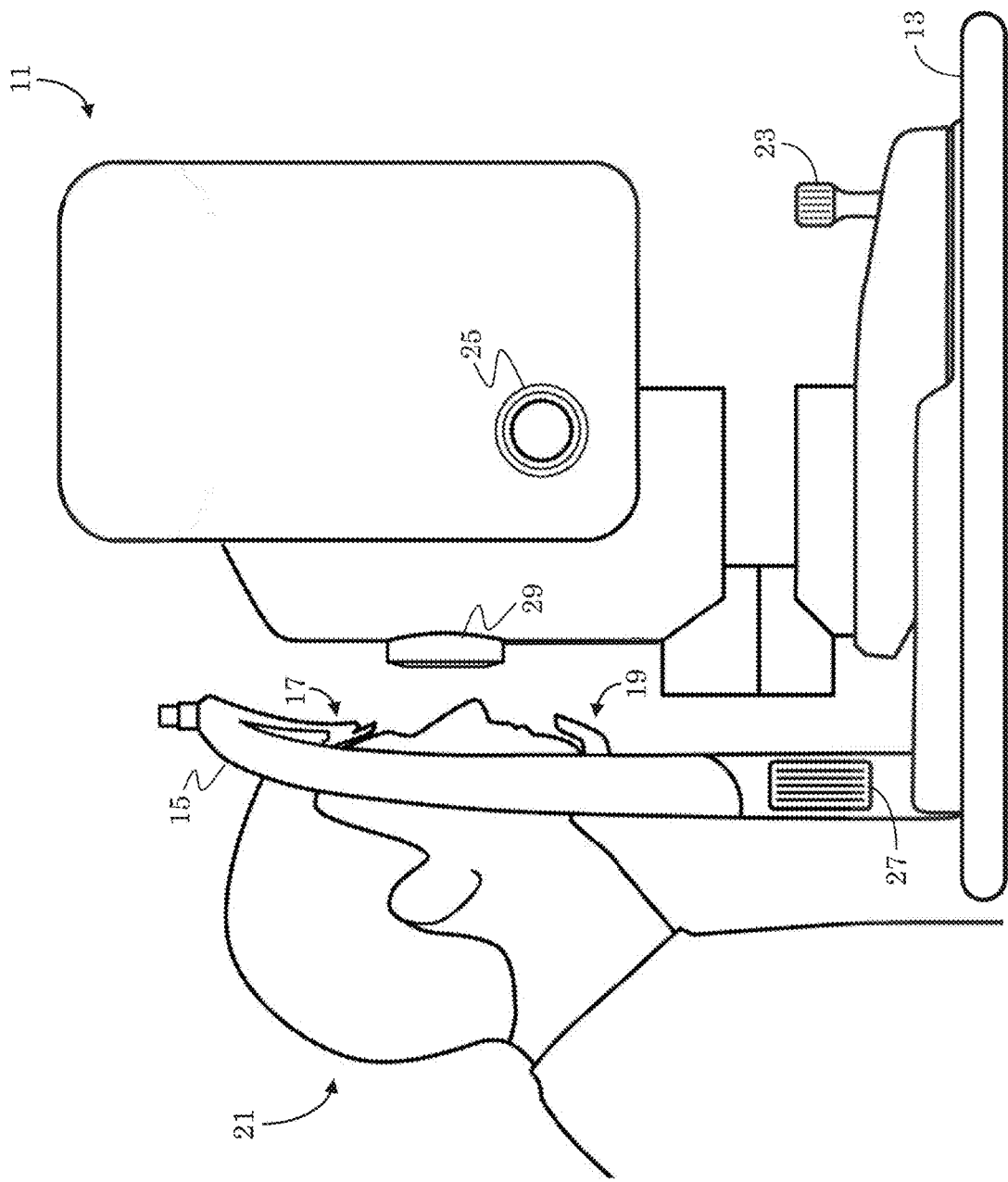
FIG. 1 shows an enclosure 11 of an ophthalmic system, such as may be found in a clinical environment.

For illustrative purposes, FIG. 1 shows an enclosure 11 of an ophthalmic system, such as may be found in a clinical environment. Enclosure 11 may house one or more types of ophthalmic systems, such as fundus imagers, OCTs, OCTAs, etc. Enclosure 11 may be positioned on a surface 13 (e.g. an adjustable table) and be coupled to a patient interface 15, which serves to position a patient 21 relative to the ophthalmic system 11. Typically, a traditional patient interface 15 may include a headrest 17 and/or a chinrest 19 for supporting the patient 21 (or subject, e.g., the patient's eye). Various portions of the instrument 11 and/or patient interface 15 may be moved relative to each other to facilitate eye alignment of the instrument 11 with the subject being imaged, for example, by using hardware controls such as joystick 23, and knobs 25 and 27. A display (e.g., an electronic screen, not shown) may also be mounted on the table 13. Ophthalmic lens 29 may serve as the instrument's aperture, such as for image acquisition. Thus, the joystick 23, knobs 25/27, and the display may be used to adjust the position of the patient interface 15 and instrument 11 to adjust patient alignment to achieve an optimal horizontal, vertical and axial position of the patient's eye-pupil relative to the system (e.g., relative to ophthalmic lens 29 and/or the system's internal optics).

The present invention seeks to facilitate the patient-to-system alignment process, and does so by eliminating the need for all (or most) alignment adjustments (or processes), be they self-alignment, operator-assisted alignment, or system-automated alignment adjustments. This is achieved by a mechanism/method that reliably and repeatedly places a patient's face in a known, predefined position relative to the ophthalmic system. One approach is to use a patient-personalized face interface (e.g. a full or partial face mask) having a molded forehead, nasal bone frame, cheek compress, and/or chin rest (or any combination therebetween) that is custom made (or custom fitted) to facial features of the patient. As described below, the combination may preferably include the nasal bone frame, which may be configured to hold a patient's nose at a predicable position (e.g., angle and position in 3D space) relative to the aperture of the ophthalmic system.

Figure 2A:
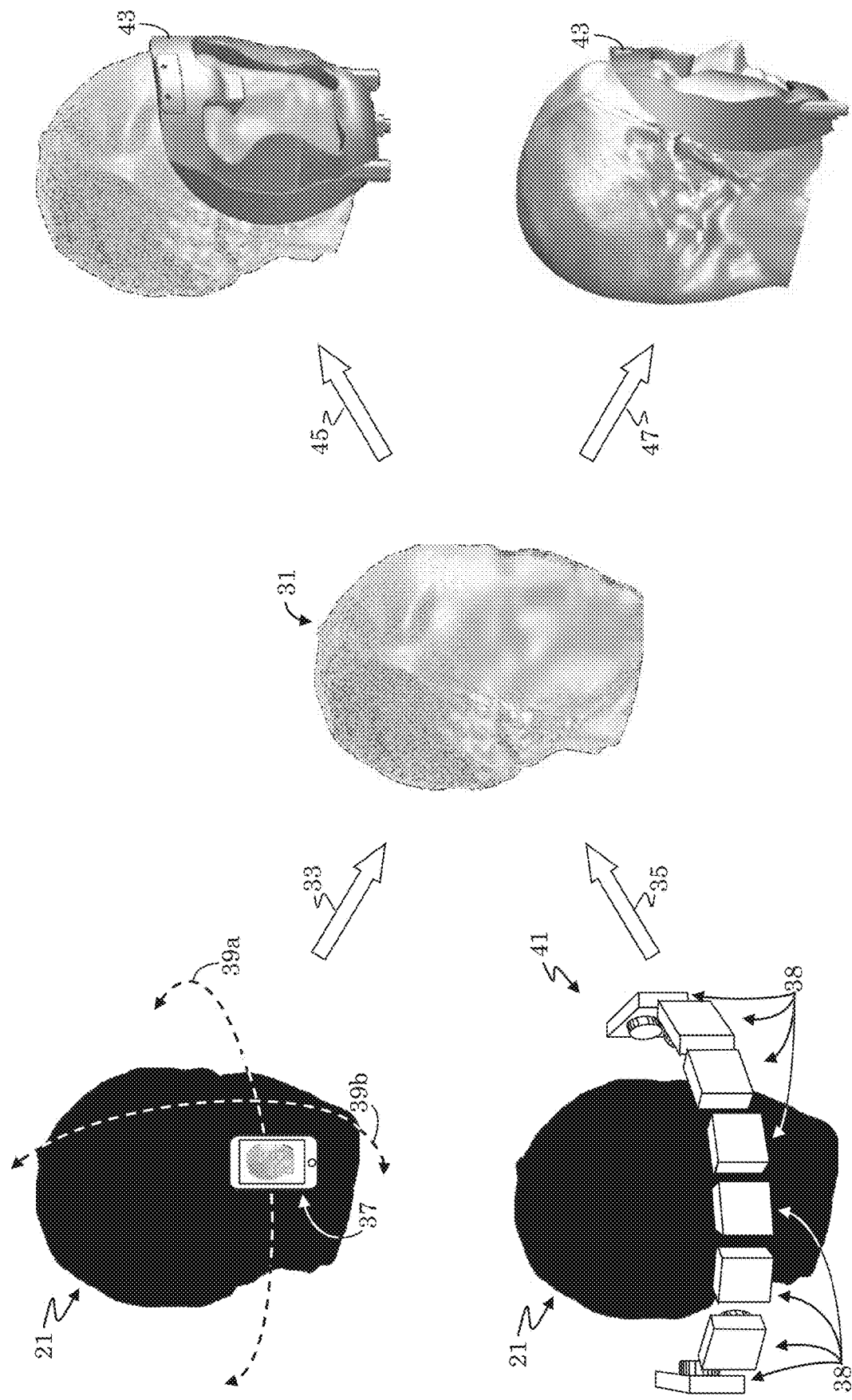
FIG. 2A illustrates a first method for providing a patient-personalized face interface in accord with the present invention.

FIG. 2A illustrates a method for providing a patient-personalized face mask in accord with the present invention. The present method may begin by acquiring a 3D model 31 of a patient 21. The 3D model 31 may be a "wireframe" or polygon mesh, e.g., a quad mesh (4 edge/vertex combinations) or triangular mesh (3 edge/vertex combinations). There are multiple methods of generating 3D model 31, two of which are illustrated in FIG. 2A, as indicated by arrows 33 and 35. A first method is to use a 3D imaging device 37, such as a depth sensing camera, which may be moved about the head of the patient 21 to scan across the patient's face and/or head, as indicated by arrows 39a and 39b. Depth sensing camera 37 may be embodied within a hand-held device, such as a smart phone or other portable computing device, such as a tablet computer or custom computing/electronic device. The hand-held device may run a 3D scanning software application (app), and/or may transmit the captured 3D data to a remote computing device (e.g., over an Internet or intranet connection) for processing and/or creation of the 3D model 31. Optionally, the 3D model 31 may be generated wholly, are partially, within the 3D imaging device 37.

Alternatively, the 3D imaging device may be embodied by a multi-camera imaging system 41. In this case, the 3D data may be obtained by (e.g., simultaneously) capturing multiple overlapping images of the patient 21 from different angles using multiple cameras 38 that preferably span the patient's face and/or head. Although one row of cameras 38 is shown, it is to be understood that multiple rows/columns of cameras (e.g., to span the upper and lower parts of the head) may be used. Again, the captured 3D data may be processed, locally or remotely, to create the 3D model 31. The remote site that processes the 3D model 31 may be accessible over a computer network, such as a local area network (LAN) or the Internet, and may be provided as a website service, for example accessible via a web browser.

The 3D imaging device may embody other 3D scanning/images technologies, singularly or in combination. For example, the 3D imaging device may embody (be based on) laser triangulation 3D scanning technology, which may project a laser beam on the face/head and measure the deformation of the laser beam. Another example is structured light 3D scanning technology, which may measure the deformation of a light pattern on the face/head to 3D scan the shape of the surface of the face/head. An additional 3D imaging technology is photogrammetry, e.g., "3D scan from photographies", which may construct a 3D model of the face/head from multiple 2D image captures (e.g., captured digital images or photographs), typically by using computer vision and computational geometry algorithms. Still another example is time-of-flight (e.g., "laser pulse") 3D scanning technology, which is based on the time of flight of a laser beam. For example, a laser beam may be projected on the face/head and collected on a sensor. The 3D geometrical information (3D model of the face/head) may be determined from the time of travel of the laser between its emission and reception. Alternatively, the 3D model may also be constructed using various mechanical approaches such as contact-based 3D scanning technology. For example, one may use a contact-based 3D scanning technology, which may use a deformation, or displacement, of a contact surface, e.g., a probe or a plurality of probes, to measure/sample several points on the face/head surface to generate the 3D model.

Irrespective of how the 3D model is acquired, a patient-personalized (e.g., patient-specific) face mask 43 may be created based on the pre-acquired 3D model 31 of the patient's face. For example, a 3D printer may be used to 3D print face mask 43, or parts thereof. Arrow 45 identifies a perspective view of an exemplary, patient-personalized full-face mask 43, and arrow 47 identifies a side view of full-face mask 43. In summary, the present approach may include creating a patient-specific 3D model 31, such as by 3D scanning the patient's face/head, and creating a physical mask 43 using the patient-specific 3D model 31 as a guide. Because the contours, structure (e.g., bone structure), size, and position of various parts of the patient's face/head (e.g., the position of an eye within an eye socket relative to the nasal bone) are known from patient-specific 3D model 31, as well as knowing what parts of a human face are generally rigid and which parts tend to be malleable or compressible (e.g., cheeks), one can create a face mask 43 that when attached to an ophthalmic device (e.g., ophthalmic diagnostic device, ophthalmic therapeutic device, ophthalmic treatment device, or ophthalmic medication dispensing device) will position the patient's eye at a desired alignment position relative to the ophthalmic device.

The thus created 3D face mask 43 may then be used as, or be a part of, or be integrated into, an existing patient interface of an ophthalmic device. Because the contours of the patient face/head are known (e.g., as determined from the patient's personalized 3D face model), and the physical properties of the ophthalmic system/device (e.g., position and orientation of the system's aperture, the systems optical path, imaging properties, etc.) are likewise known, the face mask 43 may be designed to hold the patient's head in a specific, predefined position and orientation relative to the ophthalmic device designed to provide optimal alignment to the ophthalmic device. That is, the exterior of the face mask (e.g., the outside of the mask that faces the ophthalmic device) may be personalized for a specific patient and/or for a specific ophthalmic device. For example, the exterior of the face mask may incorporate custom connectors for coupling to a specific ophthalmic devices. The position of the connectors (e.g., connector pins) and/or the exterior shape of the face mask may be configured so that the patient's pupil is always positioned to coincide with the planar center (e.g., the zero in an X-Y plane) of the ophthalmic device, such as by taking into consideration the distance between the patient's pupil and nasal bridge and/or the patient's inter-pupillary distance, and/or the size and contour of the patient's brow ridge, eye socket, nasal bridge, cheek structure, etc. The thickness and/or shape of the face mask may also be configured to the ophthalmic device so that the face mask does not interfere with (e.g., adjustments in) the working distance of the ophthalmic device. The face mask may further be designed taking patient comfort into consideration. For example, the face mask may provide for sufficient clearance between the patient and the ophthalmic device to promote comfortable breathing and to avoid creating the sensation of being constrained (e.g., avoid a claustrophobic sensation). If desired, the face mask may also be constructed such that when coupled to an ophthalmic device, the face mask shields a patient's eye from ambient light. This may enable natural dilation of the pupil of the eye. Furthermore, because the mechanical reference between face mask and the ophthalmic device is fixed, the face mask may be made to have a snug fit with the face to create a light proof enclosure. This may be beneficial in several ophthalmic applications, such as imaging/scanning ophthalmic applications. Thus, the interior of the face mask (e.g. the inside of the mask that faces the patient) may be personalized (or tied) to a specific one of multiple patients, and the exterior of the face mask may be customized for (or tied to) a specific one of multiple (e.g., types of) ophthalmic devices.

Figure 2B:
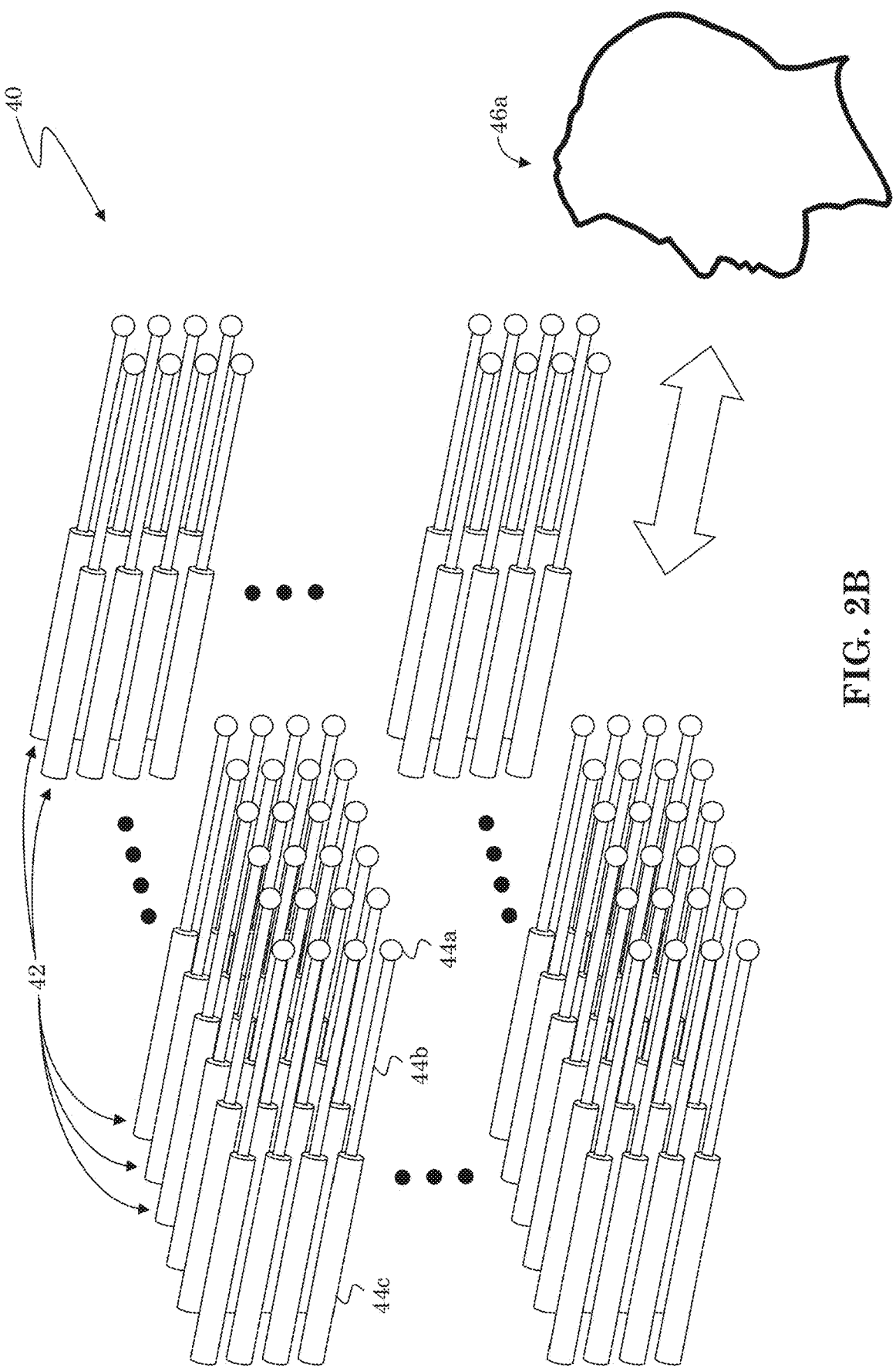
FIG. 2B and FIG. 2C illustrate a second method for providing a patient-personalized face interface in accord with the present invention.
Figure 2C:
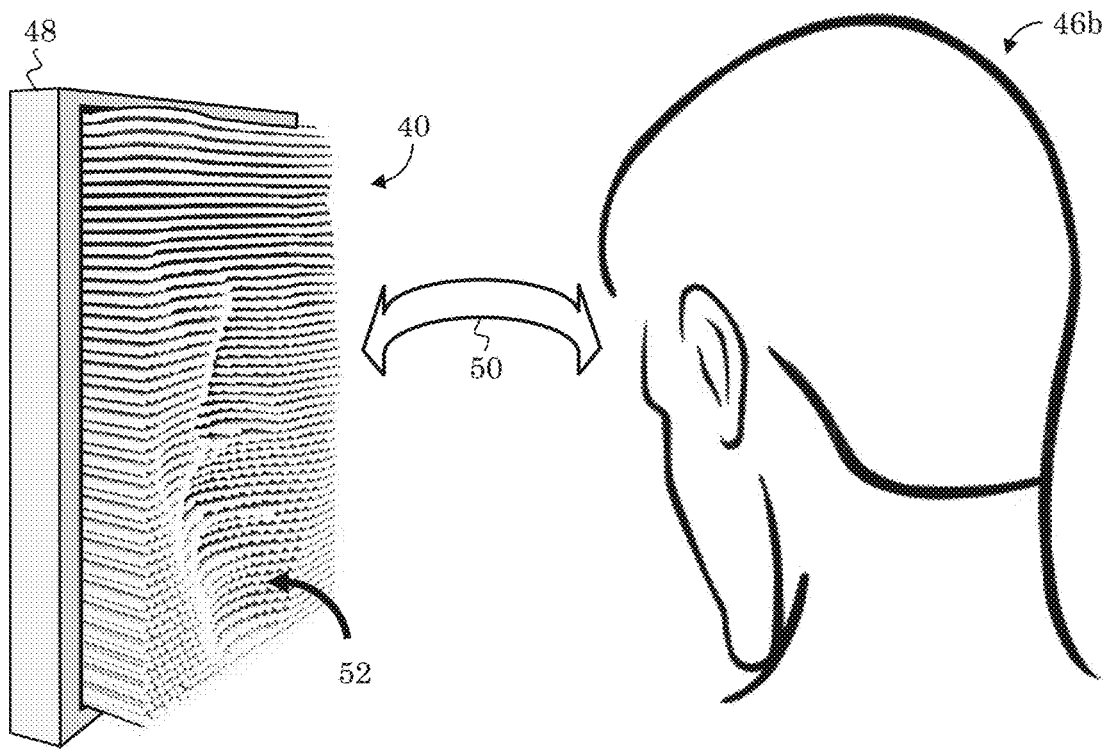
Figure 2D:
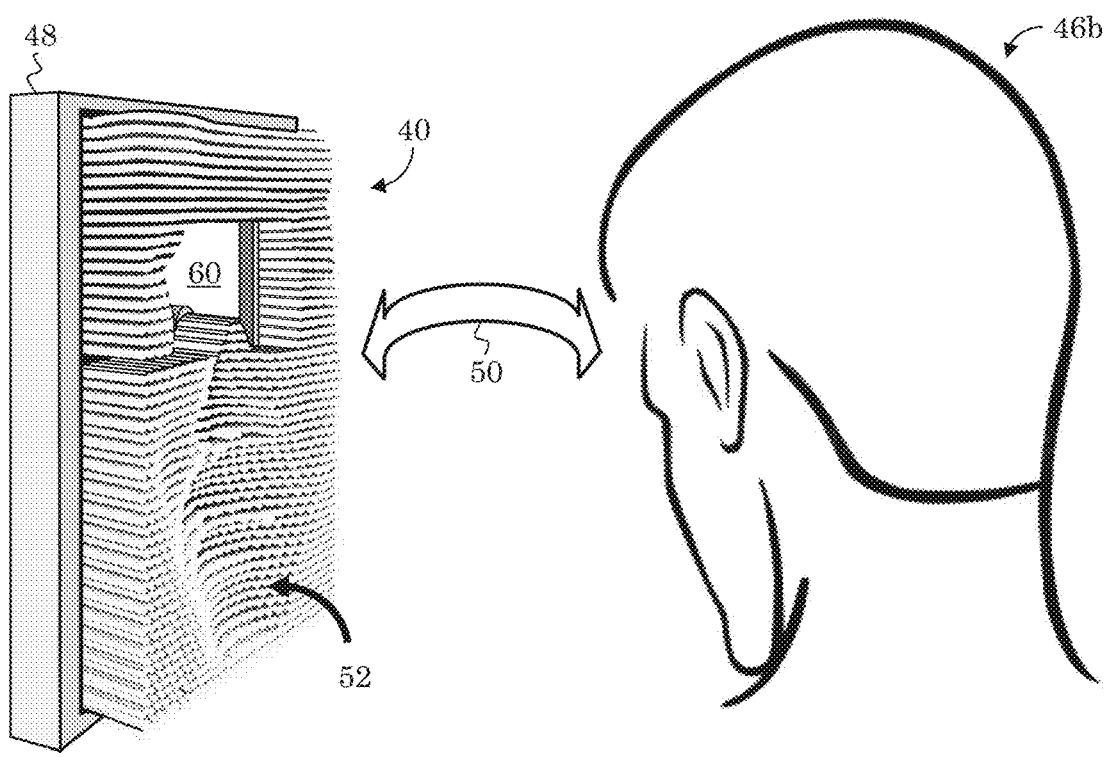
FIG. 2D illustrate the use of contact array 40 of FIG. 2B within a frame 48, and configured with an opening 60 corresponding to a patient's eye region(s) such that contact array 40 may be used as a face mask in a manner similar to face mask 63 of FIG. 2A.

FIGS. 2B and 2C illustrate another method of generating a 3D model of a face such as 3D model 31 of FIG. 2A, and FIG. 2D builds on the method of FIGS. 2B and 2C to create a custom face mask, such as face mask 43 of FIG. 2A. As is explained above, the 3D model may be defined by use of a mechanical, contact-based scanning system, but such a mechanical system may also provide, or function as, (fully or in part) the physical, patient-personalized face mask, itself. FIG. 2B shows an example of a contact-based 3D scanning system, as may be used to define the 3D model 31 of FIG. 2A. The present contact-based 3D scanning system may include a contact array 40 of individual and movable probes (e.g., pins or pistons) 42 whose contact surface (e.g., the tips 44a of piston rods 44b) may be optionally covered by a membrane (not shown). As a patient 46a presses his/her face/head into the contact array 40, different parts of the contact array 40 will be deformed/displaced differently as individual piston (or pins) 42 are pushed back (displaced) according to the contour of patient's face/head. For example, the patient's face could make contact with tip 44a (or the membrane surface over tip 44a) and push on corresponding piston rod 44b causing it to be displaced (e.g., move into an optional cylinder barrel 44c) by an amount determined by the face contour. The resultant height of each probe/piston 42 (and/or the amount of its deformation/displacement) could be detected/measured to encode the shape of the patient's face and thereby create a face scan, which may be represented as a pin/piston/probe height (displacement/deformation) map. FIG. 2C illustrates the use of contact array 40 within a frame 48. After the patient 46b has pressed/pushed his/her face into contact array 40, as indicated by curved arrow 50, the individual probe/piston/pin deformations/displacement positions 52 may be read and stored to maintain a record of the 3D scan. Optionally, the displaced positions 52 may be lockable, in place, within frame 48.

The present mechanical 3D scanning system may be adapted to function as a face mask (or part of a face mask), such as by being configured to have open areas (or translucent areas) for light from an ophthalmic system to pass through and reach a patient's eye(s). Thus, this mechanical system may not only create a 3D model of the face/head, but may also serve as a patient-personalized (e.g., patient-specific) face mask. FIG. 2D illustrates an exemplary use of contact array 40 within frame 48, which may be integrated into, or attachable to, or otherwise coupled to the enclosure 11 of an ophthalmic system (see FIG. 1), as is explained more fully below. In the present example, contact array 40 includes an opening 60 for light to pass between the eye(s) of patient 46b and the ophthalmic system. By locking the probes/piston/pin deformations 52 in place, a face mask of the patient's face/head is defined within frame 48. That is, the probe positions may be locked (and stored) to assure that the next time the patient brings his/her face to the face mask, the patient's head will be at the same position as the first time.

As stated above, the probes/pistons/pins may be covered by a membrane or other flexible piece(s) or surface(s) to create a surface similar to the 3D printed face mask 43 of FIG. 2A. It is to be understood that the present contact array 40 may be configured to capture/scan the contours of select parts of a patient's face (e.g., create a partial face mask), and/or store only probe/piston/pin displacement/deformation information for select parts of a patient's face. In this manner, if the probe displacement position data (of all, or a select portion of the pistons that correspond to the mask shape) is stored, it may be recalled when the patient comes back to the device. The probes/pistons/pins may then be moved back (manually or automatedly) to the position that was previously detected, and then locked in place. For example, the system may automatically actuate select cylinder barrels 44c of FIG. 2B (as needed according to a corresponding probe height map) to move their respective piston rods 44b to their correspondingly stored displacement positions. This recreates the exact imprint of the patient's face/head ready for use. It is to be understood that a system may store the mask information (e.g., probe height map) of multiple patients in an electronic memory, recall each patient's custom mask information, and reconfigure the mask (e.g., contact array 48) to suit the specific patient that is to use the system. Thus, the present embodiment allows multiple patients to be imaged on the same device. For each different patient, the system would call up (e.g. access from a memory store, such as a local or remote database accessible via a computer network, e.g., the Internet) the piston height map and set the device accordingly. This would allow repeated measurement of a larger population in a central testing room or station, e.g., in a nursing home or a doctor office's walk-up testing room. Optionally, once the exact shape of a patient's face/head (or target regions of the face/head, such as the temple, all or part of the nose (e.g., nasal bridge), and cheek bone) has been scanned, the present system may rotate and/or translate the face mask, or otherwise reposition the face mask, to assure that when the patient next comes in contact with the mask, the patient will be in proper alignment with the present system.

Figure 3:
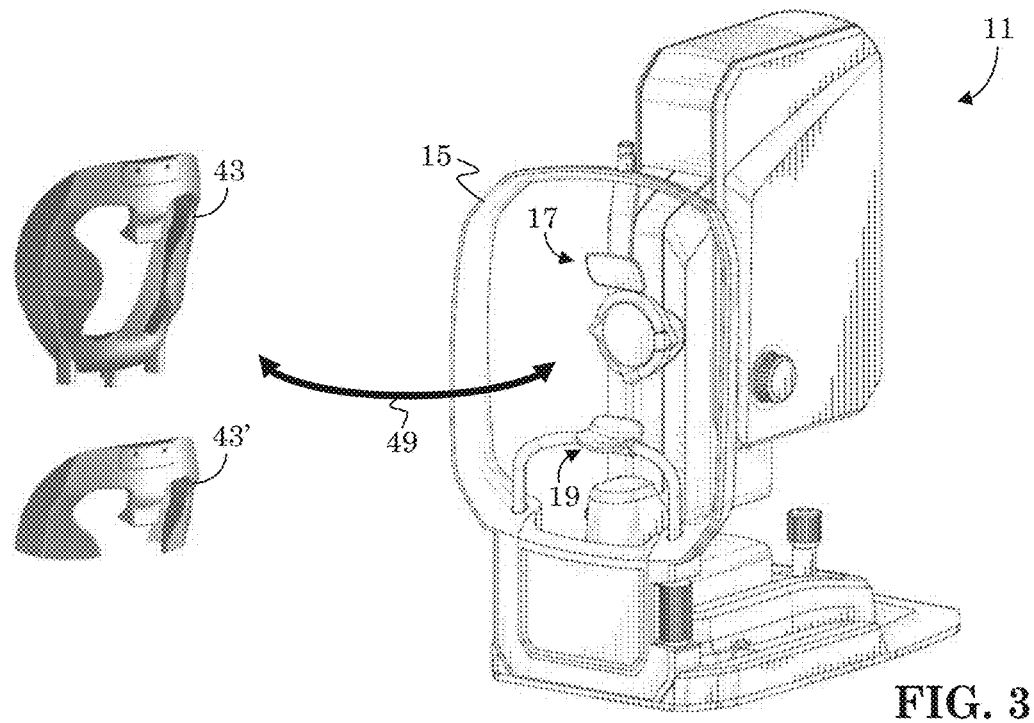
FIG. 3 shows a patient-personalized face mask incorporated (e.g., retrofitted) into the patient interface of the system 11 of FIG. 1.

For illustration purposes, FIG. 3 provides a perspective view of the enclosure 11 of FIG. 1, and a full face mask 43 or partial face mask 43' incorporated (e.g., retrofitted) into the patient interface 15 of system 11, as indicated by arrow 49. It is to be understood that unless otherwise stated or understood from context, all discussions/embodiments/features of face mask 43 and partial face mask 43' apply to the face mask defined by probe array 40. The face mask replaces the need to align the system 11 in X, Y, Z spatial directions (e.g., three-dimensional, 3D, space). If full face mask 43 is to be incorporated into patient interface 15, headrest 17 and/or a chinrest 19 may be removed and replaced by full face mask 43. In case of incorporating partial face mask 43' into patient interface 15, headrest 17 may be removed and replace by partial face mask 43', but adjustable chinrest (cup) 19 may optionally be retained and provide height adjustment as well as chinrest functionality. Alternatively, patient interface 15 may be replaced by a new patient interface based on (e.g., customized for) full face mask 43 and/or partial face mask 43'. Although partial face mask 43' is shown to include patient-specific forehead/cheek portions, it is to be understood that different partial face mask configurations are possible. Some alternate partial face mask configurations are discussed below.

Figure 4A:
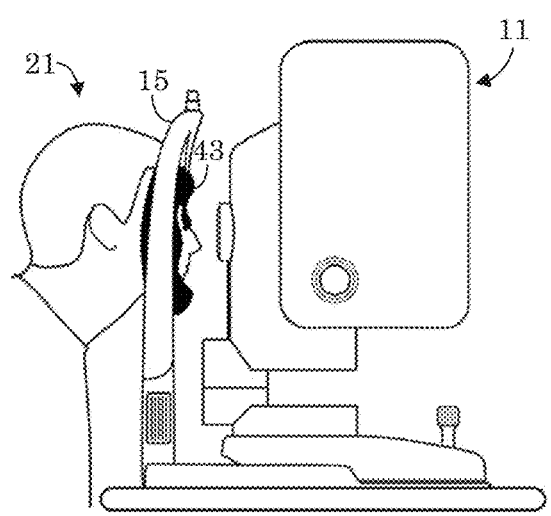
FIGS. 4a and 4b illustrate profile views of the enclosure of FIG. 3 respectively incorporating the full face mask and partial face mask of FIG. 2.
Figure 4B:
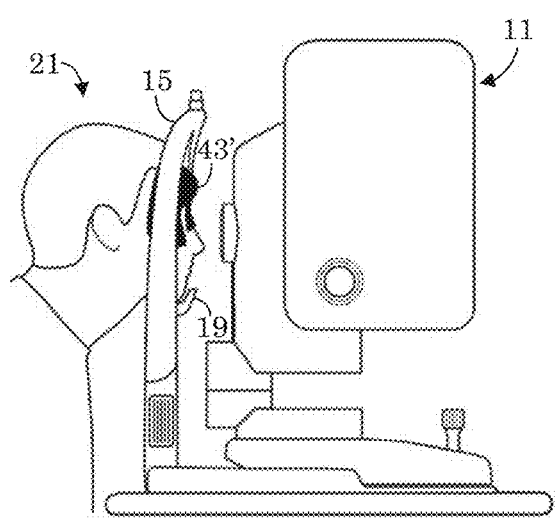

FIGS. 4a and 4b illustrate profile views of enclosure 11 of FIG. 3 respectively incorporating full face mask 43 and partial face mask 43' of FIG. 2A. In FIG. 4a, full face mask 43 is incorporated into patient interface 15 and takes the place of headrest 17 and chinrest 19 of FIG. 3. In FIG. 4b, partial face mask 43' is incorporated into patient interface 15 and takes the place of headrest 17, but patient interface 15 may still provide general height adjustment by use of chinrest cup 19. This would be an example of full face mask 43 or partial face mask 43' being used in clinical setting. In the present example, full face mask 43 and partial face mask 43' are personalized to the patient's face and used to establish a known alignment between the ophthalmic system 11 and an eye of the patient 21. That is, face masks 43 and 43' each have a preconfigured shape based on the known contours of the patient's face, as determined from the patient's pre-acquired 3D face model, and configured to hold the patient's face in a predefined position that establishes the known, and desired, alignment. Using this approach, the only task the patient 21 needs to perform is to place his/her face in either of face masks 43 or 43' to achieve alignment without, or with minimal, assistance from an operator or an automated feedback systems. Face masks 43 and 43' eliminate the need for X, Y, Z spatial adjustments to achieve proper patient-to-system alignment. The face masks 43 and 43' each have a preconfigured shape based on known contours of the patient's face and configured to hold the patient's face in a predefined position that establishes the desired, predefined alignment. Because the mask is personalized to the patient's facial contours, the patient's own comfort level is an indicator of proper alignment. That is, the patient can discern that the eye is properly aligned, and in the desired predefined position, when a number of pressure points produced by the face mask is minimized. That is, when a patient's head is properly sited in the face mask 43 or 43', pressure points on the forehead, nasal bone, temple, cheeks, and/or chin are eliminated, or minimized, making for a comfortable setting for the patient. Experimental results have achieved a repeatable alignment accuracy of 0.1 mm in all three spatial dimensions, which in the past would require much operator assistance to achieve. Thus, by use of a patient-specific mask 43 or 43', the ophthalmic system becomes pre-aligned to an individual patient without any alignment adjustments prior to the patient approaching the ophthalmic system.

Optionally, the face masks 43 and 43' may be removable and replaceable in accordance with a patient's identification. For example, a library (e.g., collection or store) of patient-specific, personalized face masks may be constructed, and a first face mask corresponding to a first patient may be removed from the patient interface 15 and replaced with a second face mask corresponding to a second patient in preparation for examining the second patient's eye. In this manner, the ease and speed of sequential examinations of different patients may be improved.

Figure 5:
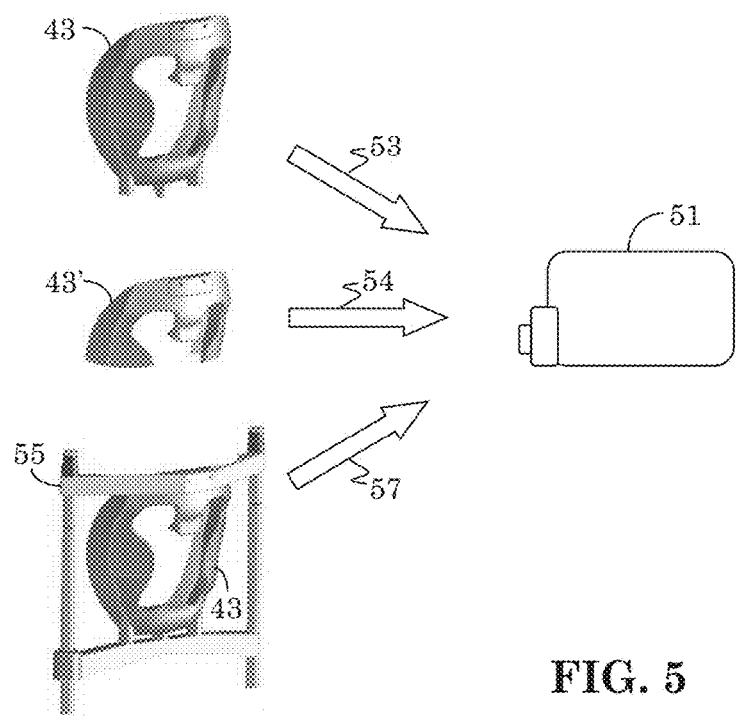
FIG. 5 illustrates an alternate, smaller profile, enclosure suitable for at-home, assisted living, or other non-clinical environments where trained system operators/technicians may not be readily available.

FIG. 5 illustrates an alternate, smaller profile, enclosure 51 suitable for application of self-administered ophthalmic procedures, such as at-home, assisted living, or other non-clinical environments where trained system operators/technicians may not be readily available. Such devices may be used to treat and/or monitor chronic or short-term maladies in a home care environment. In the present example, full face mask 43 and/or partial face mask 43' may be directly coupled to, or form an integral part of, enclosure 51, as indicated by respective arrows 53 and 54. Alternatively, either patient-specific face mask 43 or 43' may be incorporated into a patient interface (e.g., frame or support) 55, which may be part of an ophthalmic system that includes enclosure 51, as indicated by arrow 57.

Figures 6A, 6B, 6C:
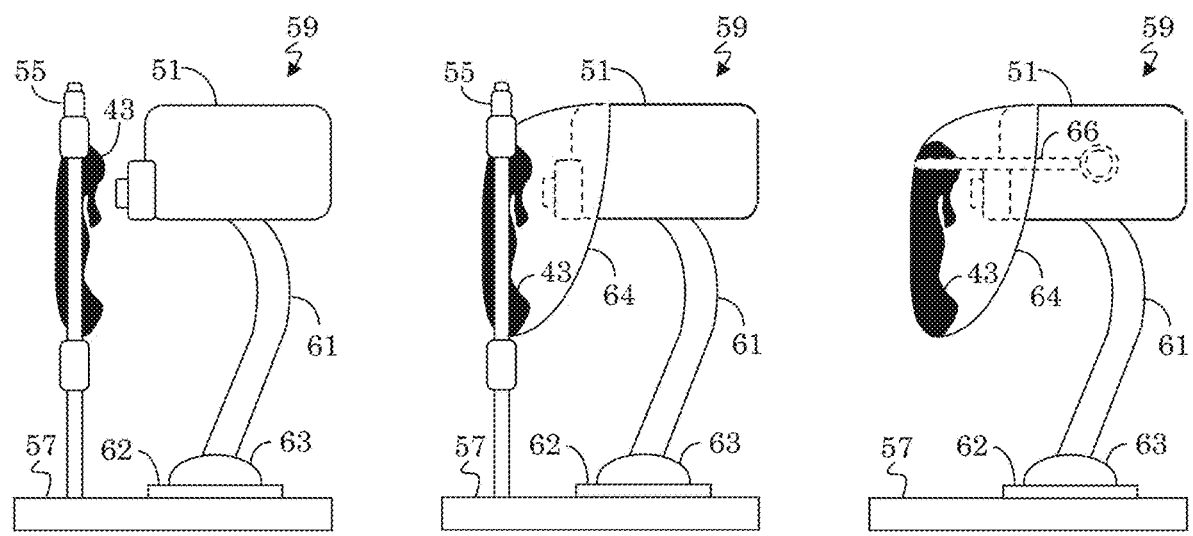
FIG. 6a illustrates a first configuration of an (at-home/portable) ophthalmic system incorporating a face mask and enclosure.
FIG. 6b illustrates a second configuration of ophthalmic system of FIG. 6a wherein a light shield extension is incorporated into the face mask or to the enclosure.
FIG. 6c illustrates a third configuration of ophthalmic system of FIG. 6a, wherein the light shield extension of FIG. 6b is rigid and provides enough structural support to couple the face mask to the ophthalmic enclosure.

FIG. 6a illustrates a first configuration of an (e.g., at-home/portable) ophthalmic system 59 incorporating face mask 43 and enclosure 51. In the present example, patient interface 55 is fixed to a base 57 of ophthalmic system 59 and holds the patient-specific face mask 43 at a position predetermined to bring a patient, not shown, into alignment with enclosure 51. Similarly, enclosure 51 may be held at a known predefined position by an arm 61 coupled to base 57. Optionally, arm 61 may be coupled to a rail and/or ratchet system 62 for translational motion (e.g., left-to-right, forward-and-backwards, up-and-down, and/or curved) and/or to a swivel hub 63 for rotational motion of enclosure 51. In this manner, the system may provide positional adjustment of enclosure 51 for better patient comfort. Alternatively, the system may be preset to a modular position determined to be appropriate for a specific patient. The system may also provide positional adjustment between predefined, and optionally lockable, positions. For example, such positions may be set to provide alternate aligned views of a patient's eye(s) (e.g., the pupil and/or retina).

FIG. 6b illustrates a second configuration of ophthalmic system 51 of FIG. 6a wherein a light shield extension 64 is incorporated into the face mask 43 or to enclosure 51. In this manner, when face mask 43 is coupled to the ophthalmic enclosure/device 51, the face mask 43 serves (e.g. may act/function as a light shield) and block ambient light.

FIG. 6c illustrates a third configuration of ophthalmic system 51 of FIG. 6a, wherein the light shield extension 64 is rigid and provides enough structural support to couple the face mask directly to the ophthalmic enclosure/device 51. In this manner patient interface 55 of FIG. 6a may be eliminated. Optionally, a support bar 66 may provide additional structural, if necessary. Support bar may further provide additional couplers to connect to face mask 43, and/or function as a rotation bar to lift face mask 43 and/or light shield extension 64 over enclosure 51.

The present ophthalmic system may be binocular (e.g., have two apertures for examining, imaging, diagnosing, treating, or medicating one or both eyes singularly or concurrently) or may be monocular (e.g., have one aperture for examining, imaging, diagnosing, treating, or medicating one eye at a time). In the case of a monocular system, enclosure 51 (or its internals, which may define an optical path) may be moved from one position to another (e.g., slide left-to-right, and vice versa) to align with one eye or the other. In a binocular system, enclosure 51 may provide two separate optical paths (one per eye, or one per aperture), or a single optical path that may selectively be directed to either eye, such as by use of a mirror switching system that selectively directs a view of either eye to the single optical path, or by use of mechanism that physically moves (e.g., translationally and/or axially) the single optical path within the enclosure 51 to be selectively aligned with one or the other of a patient's two eyes.

Figure 7A:
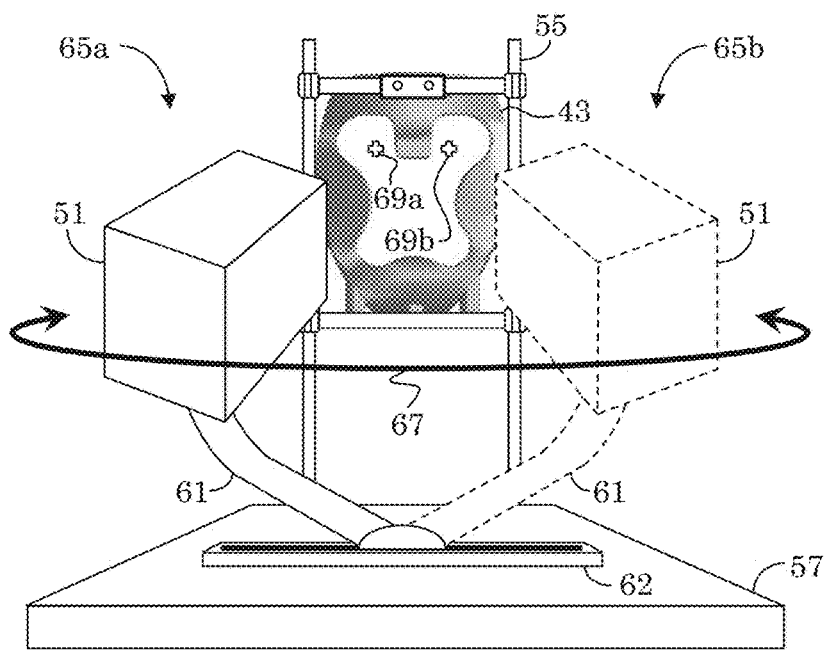
FIGS. 7a and 7b illustrate methods for aligning a monocular system with either of a patient's two eyes by moving the instrument and/or moving the patient.
Figure 7B:
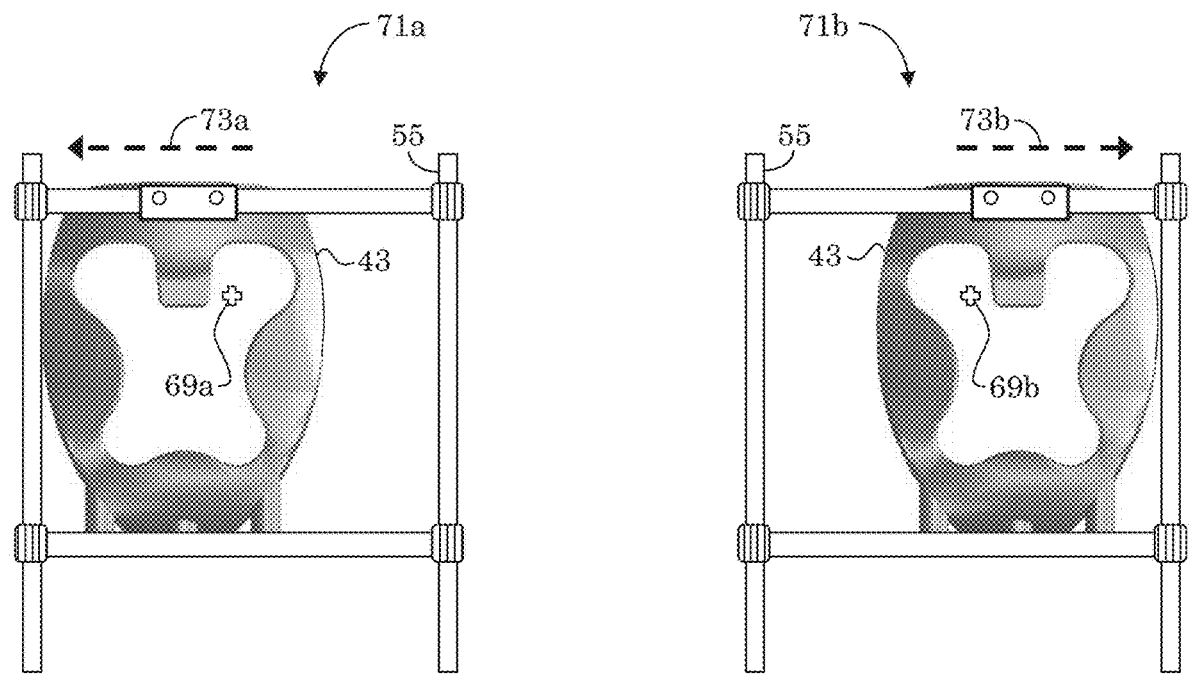

FIGS. 7a and 7b illustrate two methods for aligning a monocular system with either of a patient's two eyes. In FIG. 7a, face mask 43 is stationary and enclosure 51 may be moved between at least two (predefined) positions, each position aligning the enclosure 51 to a respective one of a patient's two eyes. In the present example, enclosure 51 may be swiveled about swivel hub 63 from a first position 65a to a second position 65b, as is indicated by arrow 67. When in position 65a, enclosure 51 is aligned with the patient's right eye, as is indicated by symbolic target crosshairs 69a. Similarly when enclosure 51 is at position 65b, as indicated by dotted outlines, enclosure 51 is aligned with the patient's right eye, which is symbolically identified by target crosshairs 69b. Alternatively, enclosure 51 may be moved laterally between positions 65a and 65b, such as by use of a rail system 62.

FIG. 7b illustrates the second method for aligning a monocular system with either of a patient's two eyes. For ease of discussion, FIG. 7b shows a frontal view of face mask 43, as part of a patient interface 55, but omits a view of the enclosure 51. It is to be understood that enclosure 51 would be stationary and positioned in front of face mask 43 in a manner similar to that of FIG. 6a. In the present embodiment, face mask 43 may be moved between at least two (predefined) positions while enclosure 51 remains stationary in front of the face mask 43. For example, face mask 43 may be moved (e.g., slid along rails of the patient interface 55) according to arrow 73a to a first position 71a that aligns the patient's left pupil 69a with an aperture of enclosure 51, and may be moved to a second position 71b according to arrow 73b that aligns the patient's right pupil 69b with the same aperture of enclosure 51.

Figure 8A:
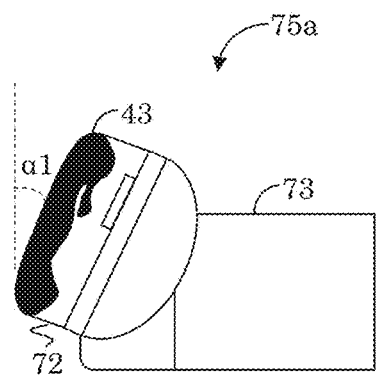
FIGS. 8a, 8b, and 8c illustrate alternate embodiment(s) of ophthalmic system(s) in accord with the present invention, where the face mask may be positioned at one, or multiple different, off-vertical inclined angle(s) relative to an ophthalmic device enclosure 73.
Figure 8B:
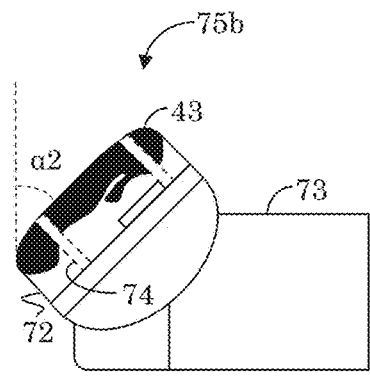
Figure 8C:
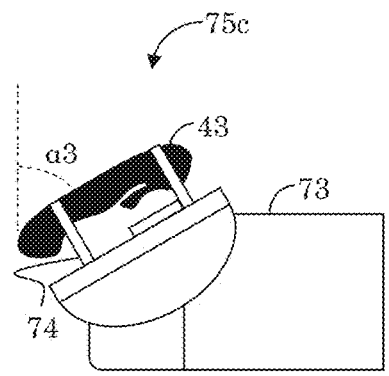

FIGS. 8a, 8b, and 8c illustrate alternate embodiment(s) of ophthalmic system(s) in accord with the present invention, where the face mask 43 may be positioned at one, or multiple different, off-vertical inclined angle(s) relative to an ophthalmic device enclosure 73. The embodiments of FIGS. 8a and 8b include a light shield 72 similar to that of FIG. 6C. In FIG. 8a, the light shield 72, which may be part of face mask 43, directly couples and supports the face mask 43 to the ophthalmic device enclosure 73. In FIG. 8b, optional support bars 74 are provided to help couple face mask 43 to the ophthalmic device enclosure 73. FIGS. 8a-8c provide three different examples 75a, 75b, and 75c of face mask 43 at three respectively different incline angles $\alpha 1$, $\alpha 2$, and $\alpha 3$ are shown. As it would be understood, each angle would require a different level of inclination by a patient to place the patient's face into face mask 43. A patient may find one angle of inclination more comfortable than another, and the ophthalmic system may be configured to present face mask 43 at an angle comfortable for a given patient, or for a group of patients. The angle may be fixed or adjustable.

Figure 9A:
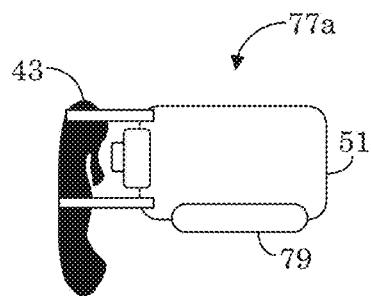
FIGS. 9a and 9b provides two configurations of an alternate embodiment wherein an ophthalmic system in accord with the present invention has a handheld configuration, and the face mask is directly coupled to the enclosure without the use of a table base.
Figure 9B:
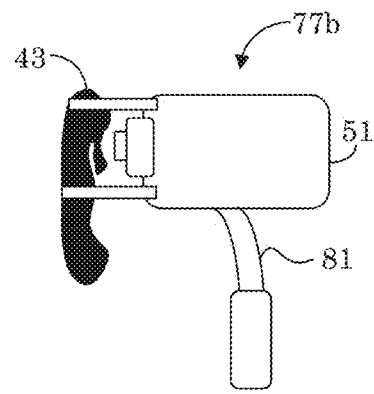

FIG. 9 provides two configurations, 77a and 77b, of an alternate embodiment wherein an ophthalmic system in accord with the present invention has a handheld configuration, and face mask 43 is directly coupled to the enclosure 51 without the use of a table base. This configuration may be beneficial when the ophthalmic device is lightweight, and graspable by one or two hands. Optionally, handhold(s) 79 (in embodiment 77a) or handle(s) 81 (in embodiment 77b) may be provided for ease of gripping and positioning by a patient. In this manner, the ophthalmic device may be used in an inclined or reclined position without unduly burdening a bedridden patient. That is, the ophthalmic device may be determined to be in proper alignment when, in a resting position, it presses comfortably against the patient's face.

Figure 10A:
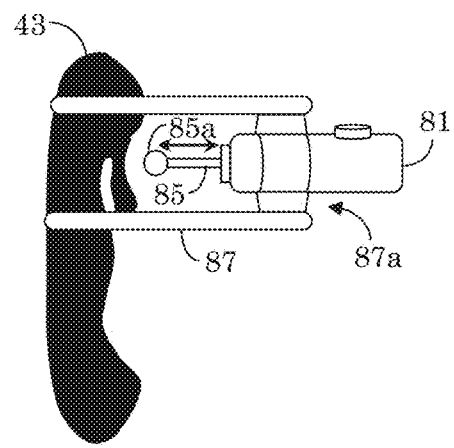
FIGS. 10a and 10b show ophthalmic device enclosures directly coupled to a face mask.
Figure 10B:
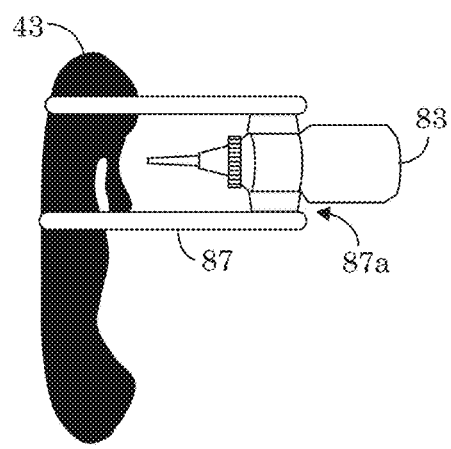

Optionally, face mask 43 may comprise the entirety, or the majority, of the patient interface. For example, FIGS. 10a and 10b show ophthalmic device enclosures directly coupled to the face mask 43. This construct may be preferable in situations where an ophthalmic device enclosure is small, such as when it houses a tonometer 81, as shown in FIG. 10a, and/or an eye medication (e.g. eye drop) dispenser 83, as shown in FIG. 10b.

Tonometers measure the pressure in an eye (intraocular pressure), which may be of particular interest to patients suffering from glaucoma. A glaucoma is the excavation (excision) of the optic nerve. This typically results in steadily progressing damage to the optic nerve, leading to an equally steady reduction of the visual field of a patient. Without therapy, this may result in loss of eyesight. Although the exact cause of glaucoma or damage to the optic nerve is not fully understood, an increase in intraocular pressure has been identified as a likely indicator.

Medication application and intraocular pressure (IOP) monitoring at home are thus integral parts of glaucoma care. Both require fine motor skills and continuous patient adherence over many years since one typically lives with the disease into an advanced age. But it can be difficult for a patient to adhere to a strict monitoring and medication regiment without assistance. Self-administered medication, in particular eye drop application, has been shown to have poor patient adherence and unsuccessful drop administration outcomes. The global increase of chronic disease (along with its associated burden on health care systems) will likely increase demand for patient self-management. One reason for poor adherence may be the heretofore difficulty associated with the use of such ophthalmic devices.

FIG. 10a shows a tonometer 81 based on a rebound measuring principle, in which a probe (e.g., a rod) 85 moves in-and-out to rebound repeatedly on an eyeball (e.g., the rod tip 85a is repeated thrusted at the eyeball and allowed to bounce back) to measure intraocular pressure. This device permits IOP monitoring outside a clinic, which provides more information to the ophthalmologist. FIG. 10b shows a medication applicator base on a drop delivery system using a medication bottle 83. Other drug delivery systems (e.g., for topical medication) may include a probe that applies ophthalmic medication by touching an eye in a manner similar to probe 85 of tonometer 81 or a piezoelectric drug delivery system that ejects droplets of medication to an eye.

Irrespective, such ophthalmic devices are typically hand-held, and it can be difficult, particularly for the elderly or for anyone who does not have a steady hand, to self-administer a medical procedure that requires bringing a hand-held ophthalmic device in close proximity to, or in contact with, one's eye. By virtue of attaching the typically hand-held ophthalmic device to a patient-specific face mask 43, the patient can bring the ophthalmic device (e.g., tonometer 81 or medication bottle 83) to his/her eye with confidence since the face mask 43 maintains the ophthalmic device at a predefined and safe distance from the patient's eye.

The present configuration also simplifies the use of the present system in a reclining position, as may be preferred when applying ophthalmic medication by use of a squeeze-activated drop bottle, a manual electronic-activated (e.g., piezoelectric or piezo printing) medication dispenser, or an automatic electric/electronic medication dispenser that automatically dispenses medication when it senses that the eye ball is available, such as may be determined by use of a camera.

Optionally, the coupling mechanism (e.g., connector arm) 87 for connecting/coupling face mask 43 to an enclosure (e.g., tonometer 81 or medication bottle 83) may have a modular, or flexible, end 87a to receive different types of enclosures (e.g., tonometer 81 or medication bottle 83), and thus different types of ophthalmic devices. In this manner, a patient may be presented with a single face mask 43 to which the patient may selectively (interchangeably) attach any one of multiple ophthalmic devices, such as tonometer 81 or ophthalmic device medication dispenser 83.

Some of the above described embodiments show the use of a full-face, patient-specific face mask 43, but all embodiments may be implemented with a full or a partial face mask. FIGS. 11a to 11e provide various examples of partial face masks. In all of these configuration, the portion of a face mask that are used may be configured to align to one or more boney section of the patient's face, and optionally only to the bony section(s). FIG. 11a illustrates a two-piece, partial face mask 91 including an upper portion 91a and a lower portion 91b. Upper portion 91a may span a first region R1 configured to align to a patient's forehead (and optionally the patient's temple region) and a second region R2 configured to align to the patient's nasal bone region. Lower portion 91b may span the chin (and lower jaw bone) of the patient.

Figure 11B:
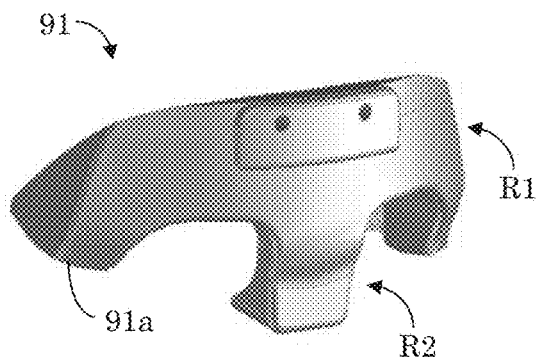
FIGS. 11a to 11e provide various examples of partial face masks in accord with the present invention.
Figure 11B:
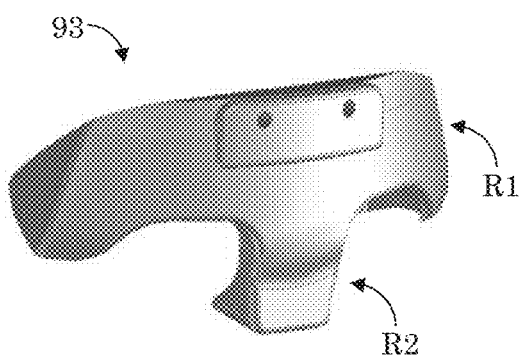
Figure 11A:
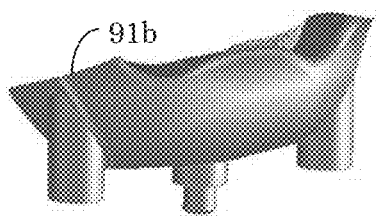

FIG. 11b shows an alternate one-piece, partial face mask 93 spanning the forehead region R1 and nasal bone region R2 in a manner similar to that of FIG. 11a. If a partial face mask were coupled to a patient interface, for example as illustrated in FIGS. 3 to 6, then the portion(s) of the patient's face not covered by the face mask may be fitted to the patient interface. For example, a patient interface may provide an adjustable chinrest, such as shown in FIG. 3, and the chin rest may be fitted to the patient with the patient's face fitted in the face mask.

Figure 11C:
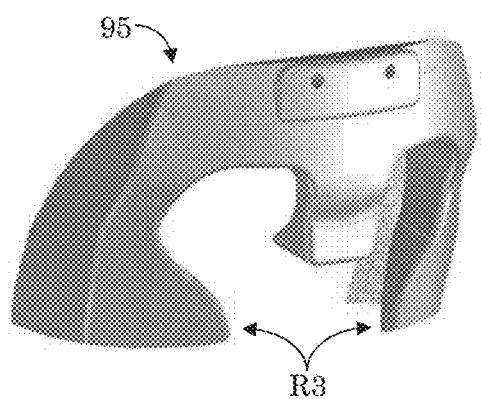
Figure 11D:
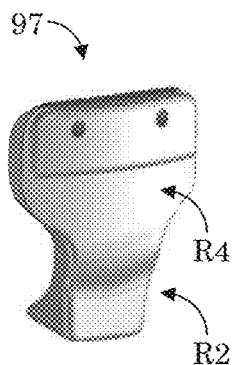

FIG. 11c illustrate still another one-piece, partial face mask 95 that enlarges the coverage of partial face mask 93 to at least partially include the patient's cheek region R3. A third one-piece configuration is shown in FIG. 11d, which limits the mask coverage to the nose region R2 (nasal bridge and optionally at least part of the nasal cartridge) and the supraorbital ridge (e.g., brow ridge) R4.

Figure 11E:
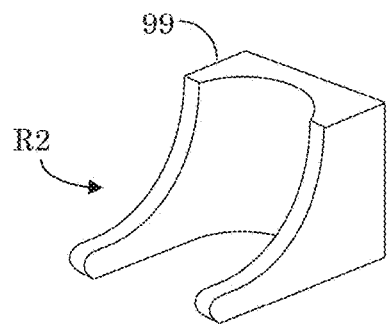

Optionally, all partial face mask configurations include at least a patient's nasal bone region. With reference to FIG. 11e, the portion 99 of a face mask that is configured to a patient's nose region R2 is effective for assuring that a patients face (and thus the patient's eye) is at predefined position (and angle) for proper alignment. Although portion 99 preferably does not pinch the patient' nose, proper alignment is improved by the patient comfortably inserting his/her nose into portion 99. Having a face mask that covers other regions in addition to a patient's nose is helpful for providing the patient with additional contact points as points of reference.

In the case of the present face mask being incorporated into an ophthalmic system that depends on a select view of the patient's retina, such as fundus imager or OCT-based systems, critical alignment specifications may be required. In such cases, it may be beneficial to provide an additional refinement technique for the alinement. This refinement technique may be provided simply by the patient changing their gaze direction without additional mechanical adjustment of the patient's position. In this situation, gaze adjustment may be provided by inclusion of a fixation target in the ophthalmic system. The fixation target (e.g., a fixation light or light pattern) provides the patient with something to stare at, and thereby directs the patient's gaze to a desired direction. A more detailed description of a fixation target is proved below.

Hereinafter is provided a description of various hardware and architectures suitable for the present invention.

Visual Field Test System

Figure 12:
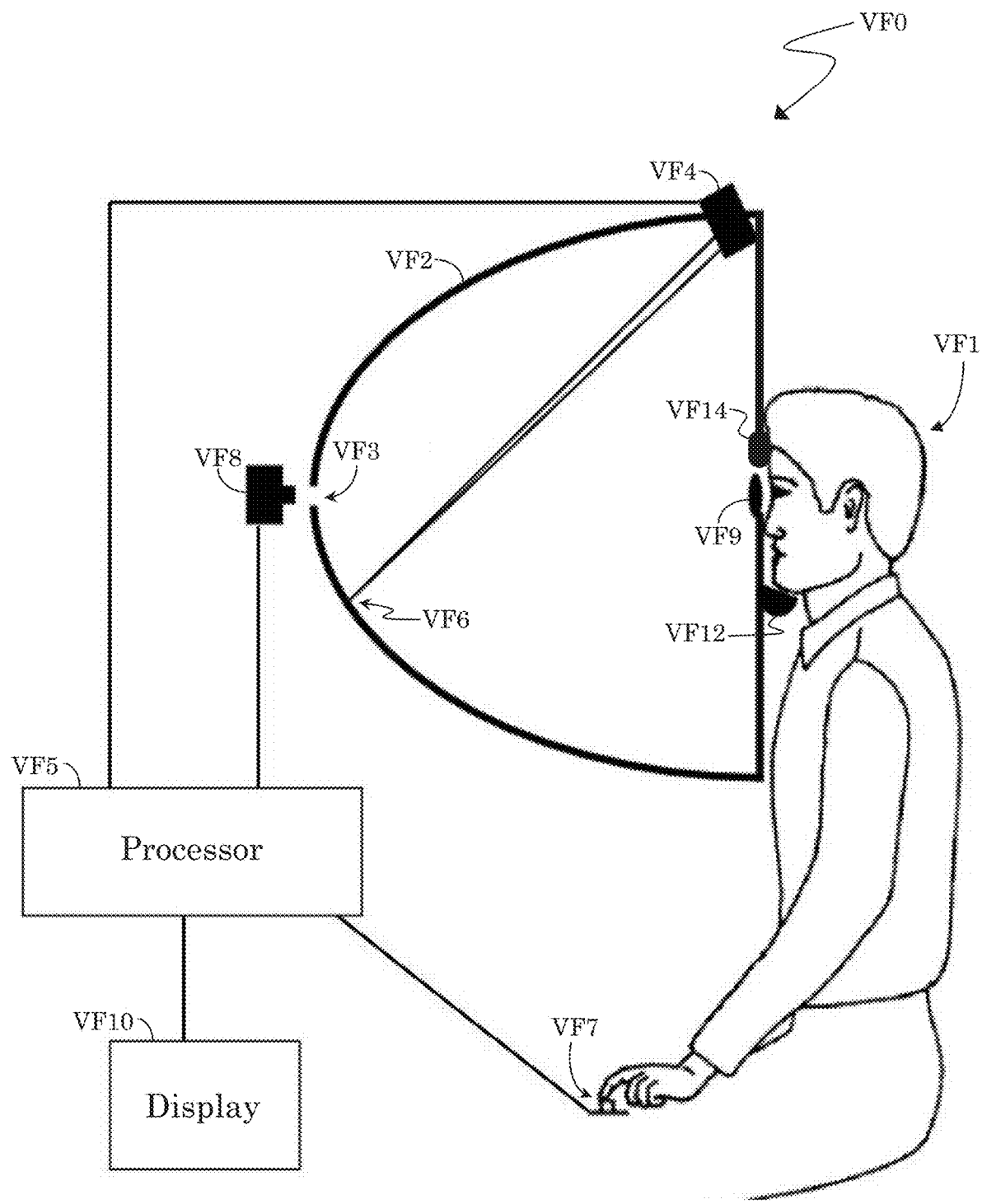
FIG. 12 illustrates an example of a visual field test instrument (perimeter) for testing a patient's visual field.

The improvements described herein may be used in conjunction with any type of visual field tester/system, e.g., perimeter. One such system is a "bowl" visual field tester VF0, as illustrated in FIG. 12. A subject (e.g., patient) VF1 is shown observing a hemispherical projection screen (or other type of display) VF2 generally shaped as a bowl, for which the tester VF0 is so termed. Typically, the subject is instructed to fixate at a point at the center of the hemispherical screen VF3. The subject rests his/her head on a patient support, which may include a chin rest VF12 and/or a forehead rest VF14. For instance, the subject rests his/her head on the chin rest VF12 and places his/her forehead against the forehead rest VF14. Optionally, the chin rest VF12 and the forehead rest VF14 may be moved together or independently of one another to correctly fixate/position the patient's eye, e.g., relative to a trial lens holder VF9 that may hold a lens through which the subject may view screen VF2. For example, the chin rest and headrest may move independently in the vertical direction to accommodate different patient head sizes and move together in the horizontal and/or vertical direction to correctly position the head. However, this is not limiting, and other arrangements/movements can be envisioned by one skilled in the art.

A projector, or other imaging device, VF4 under control of a processor VF5 displays a series of test stimuli (e.g., test points of any shape) VF6 onto the screen VF2. The subject VF1 indicates that he/she sees a stimulus VF6 by actuating a user input VF7 (e.g., depressing an input button). This subject response may be recorded by processor VF5, which may function to evaluate the visual field of an eye based on the subject's responses, e.g., determine the size, position, and/or intensity of a test stimulus VF6 at which it can no longer be seen by the subject VF1, and thereby determine the (visible) threshold of the test stimulus VF6. A camera VF8 may be used to capture the gaze (e.g., gaze direction) of the patient throughout the test. Gaze direction may be used for patient alignment and/or to ascertain the patient's adherence to proper test procedures. In the present example, the camera VF8 is located on the Z-axis relative to the patient's eye (e.g. relative to trial lens holder VF9) and behind the bowl (of screen VF2) for capturing live images(s) or video of the patient's eye. In other embodiments, this camera may be located off this Z-axis. The images from the gaze camera VF8 can optionally be displayed on a second display VF10 to a clinician (who may also be interchangeably referred to herein as a technician) for aid in patient alignment or test verification. The camera VF8 may record and store one or more images of the eye during each stimulus presentation. This may lead to a collection of anywhere from tens to hundreds of images per visual field test, depending on the testing conditions. Alternatively, the camera VF8 may record and store a full length movie during the test and provide time stamps indicating when each stimulus is presented. Additionally, images may also be collected between stimulus presentations to provide details on the subject's overall attention throughout the VF test's duration.

Trial lens holder VF9 may be positioned in front of the patient's eye to correct for any refractive error in the eye. Optionally, the lens holder VF9 may carry or hold a liquid trial lens (see for example U.S. Pat. No. 8,668,338, the contents of which are hereby incorporated in their entirety by reference), which may be utilized to provide variable refractive correction for the patient VF1. However, it should be noted that the present invention is not limited to using a liquid trial lens for refraction correction and other conventional/standard trial lenses known in the art may also be used.

In some embodiments, one or more light sources (not shown) may be positioned in front of the eye of the subject VF1, which create reflections from ocular surfaces such as the cornea. In one variation, the light sources may be light-emitting diodes (LEDs).

While FIG. 12 shows a projection type visual field tester VF0, the invention described herein may be used with other types of devices (visual field testers), including those that generate images through a liquid crystal display (LCD) or other electronic display (see for example U.S. Pat. No. 8,132,916, hereby incorporated by reference). Other types of visual field testers include, for example, flat-screen testers, miniaturized testers, and binocular visual field testers. Examples of these types of testers may be found in U.S. Pat. Nos. 8,371,696, 5,912,723, 8,931,905, U.S. designed Pat. D472637, each of which is hereby incorporated in its entirety by reference.

Visual field tester VF0 may incorporate an instrument-control system (e.g. running an algorithm, which may be software, code, and/or routine) that uses hardware signals and a motorized positioning system to automatically position the patient's eye at a desired position, e.g., the center of a refraction correction lens at lens holder VF9. For example, stepper motors may move chin rest VF12 and the forehead rest VF14 under software control. A rocker switch may be provided to enable the attending technician to adjust the patient's head position by causing the chin rest and forehead stepper motors to operate. A manually moveable refraction lens may also be placed in front of the patient's eye on lens holder VF9 as close to the patient's eye as possible without adversely affecting the patient's comfort. Optionally, the instrument control algorithm may pause perimetry test execution while chin rest and/or forehead motor movements are under way if such movements would disrupt test execution.

Fundus Imaging System

Two categories of imaging systems used to image the fundus are flood illumination imaging systems (or flood illumination imagers) and scan illumination imaging systems (or scan imagers). Flood illumination imagers flood with light an entire field of view (FOV) of interest of a specimen at the same time, such as by use of a flash lamp, and capture a full-frame image of the specimen (e.g., the fundus) with a full-frame camera (e.g., a camera having a two-dimensional (2D) photo sensor array of sufficient size to capture the desired FOV, as a whole). For example, a flood illumination fundus imager would flood the fundus of an eye with light, and capture a full-frame image of the fundus in a single image capture sequence of the camera. A scan imager provides a scan beam that is scanned across a subject, e.g., an eye, and the scan beam is imaged at different scan positions as it is scanned across the subject creating a series of image-segments that may be reconstructed, e.g., montaged, to create a composite image of the desired FOV. The scan beam could be a point, a line, or a two-dimensional area such a slit or broad line.

Figure 13:
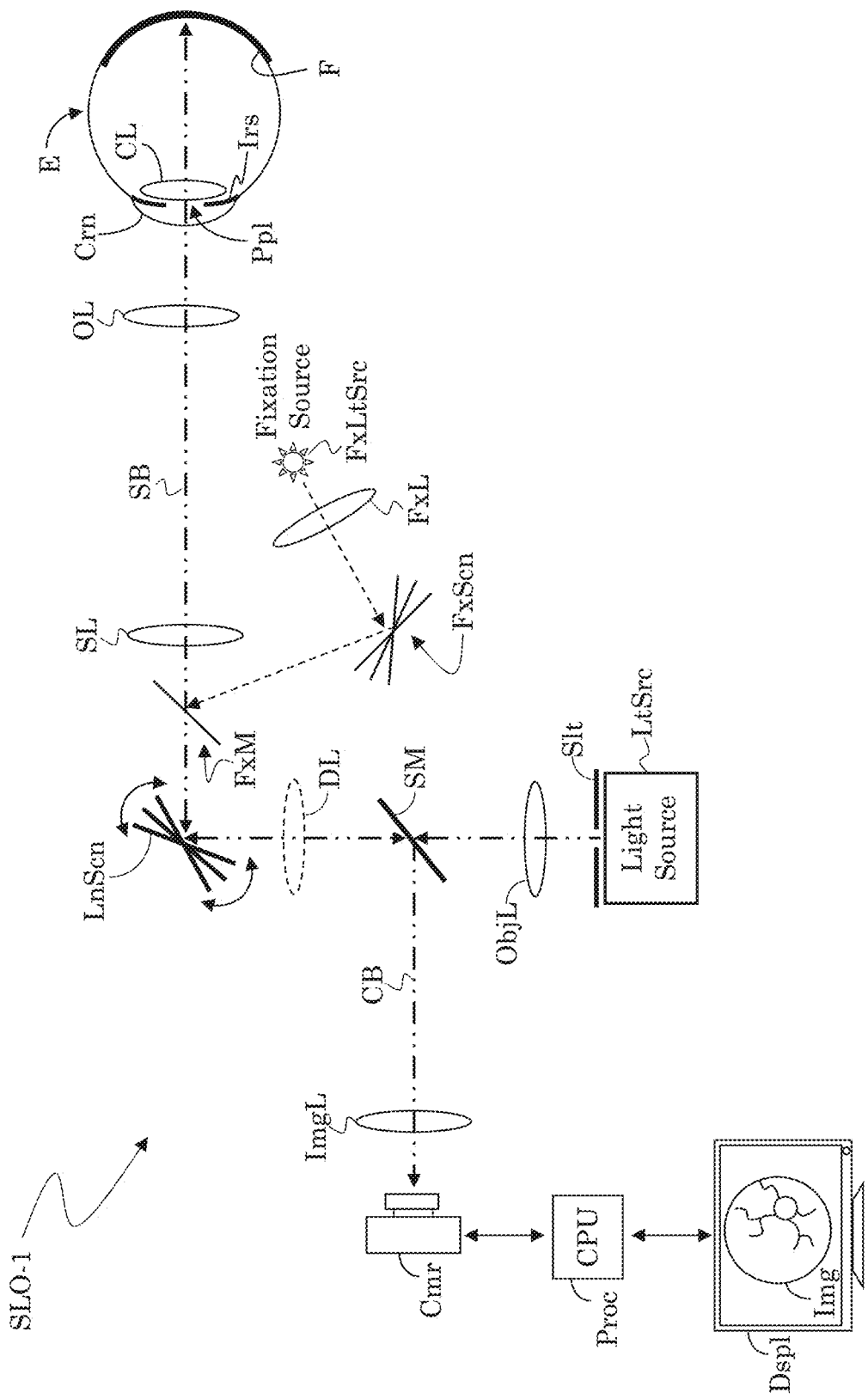
FIG. 13 illustrates an example of a slit scanning ophthalmic system for imaging a fundus.

FIG. 13 illustrates an example of a slit scanning ophthalmic system SLO-1 for imaging a fundus F, which is the interior surface of an eye E opposite the eye lens (or crystalline lens) CL and may include the retina, optic disc, macula, fovea, and posterior pole. In the present example, the imaging system is in a so-called "scan-descan" configuration, wherein a scanning line beam SB traverses the optical components of the eye E (including the cornea Crn, iris Irs, pupil Ppl, and crystalline lens CL) to be scanned across the fundus F. In the case of a flood fundus imager, no scanner is needed, and the light is applied across the entire, desired field of view (FOV) at once. Other scanning configurations are known in the art, and the specific scanning configuration is not critical to the present invention. As depicted, the imaging system includes one or more light sources LtSrc, preferably a multi-color LED system or a laser system in which the etendue has been suitably adjusted. An optional slit Slt (adjustable or static) is positioned in front of the light source LtSrc and may be used to adjust the width of the scanning line beam SB. Additionally, slit Slt may remain static during imaging or may be adjusted to different widths to allow for different confocality levels and different applications either for a particular scan or during the scan for use in suppressing reflexes. An optional objective lens ObjL may be placed in front of the slit Slt. The objective lens ObjL can be any one of state-of-the-art lenses including but not limited to refractive, diffractive, reflective, or hybrid lenses/systems. The light from slit Slt passes through a pupil splitting mirror SM and is directed towards a scanner LnScn. It is desirable to bring the scanning plane and the pupil plane as near together as possible to reduce vignetting in the system. Optional optics DL may be included to manipulate the optical distance between the images of the two components. Pupil splitting mirror SM may pass an illumination beam from light source LtSrc to scanner LnScn, and reflect a detection beam from scanner LnScn (e.g., reflected light returning from eye E) toward a camera Cmr. A task of the pupil splitting mirror SM is to split the illumination and detection beams and to aid in the suppression of system reflexes. The scanner LnScn could be a rotating galvo scanner or other types of scanners (e.g., piezo or voice coil, micro-electromechanical system (MEMS) scanners, electro-optical deflectors, and/or rotating polygon scanners). Depending on whether the pupil splitting is done before or after the scanner LnScn, the scanning could be broken into two steps wherein one scanner is in an illumination path and a separate scanner is in a detection path. Specific pupil splitting arrangements are described in detail in U.S. Pat. No. 9,456,746, which is herein incorporated in its entirety by reference.

From the scanner LnScn, the illumination beam passes through one or more optics, in this case a scanning lens SL and an ophthalmic or ocular lens OL, that allow for the pupil of the eye E to be imaged to an image pupil of the system. Generally, the scan lens SL receives a scanning illumination beam from the scanner LnScn at any of multiple scan angles (incident angles), and produces scanning line beam SB with a substantially flat surface focal plane (e.g., a collimated light path). Ophthalmic lens OL may focus the scanning line beam SB onto the fundus F (or retina) of eye E and image the fundus. In this manner, scanning line beam SB creates a traversing scan line that travels across the fundus F. One possible configuration for these optics is a Kepler type telescope wherein the distance between the two lenses is selected to create an approximately telecentric intermediate fundus image (**4-*f*** configuration). The ophthalmic lens OL could be a single lens, an achromatic lens, or an arrangement of different lenses. All lenses could be refractive, diffractive, reflective or hybrid as known to one skilled in the art. The focal length(s) of the ophthalmic lens OL, scan lens SL and the size and/or form of the pupil splitting mirror SM and scanner LnScn could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. For example, a 45° to 60° field of view is a typical, or standard, FOV for fundus cameras. Higher fields of view, e.g., a widefield FOV, of 60°-120°, or more, may also be feasible. A widefield FOV may be desired for a combination of the Broad-Line Fundus Imager (BLFI) with another imaging modalities such as optical coherence tomography (OCT). The upper limit for the field of view may be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The scanning line beam SB passes through the pupil Ppl of the eye E and is directed towards the retinal, or fundus, surface F. The scanner LnScn1 adjusts the location of the light on the retina, or fundus, F such that a range of transverse locations on the eye E are illuminated. Reflected or scattered light (or emitted light in the case of fluorescence imaging) is directed back along as similar path as the illumination to define a collection beam CB on a detection path to camera Cmr.

In the "scan-descan" configuration of the present, exemplary slit scanning ophthalmic system SLO-1, light returning from the eye E is "descanned" by scanner LnScn on its way to pupil splitting mirror SM. That is, scanner LnScn scans the illumination beam from pupil splitting mirror SM to define the scanning illumination beam SB across eye E, but since scanner LnScn also receives returning light from eye E at the same scan position, scanner LnScn has the effect of descanning the returning light (e.g., cancelling the scanning action) to define a non-scanning (e.g., steady or stationary) collection beam from scanner LnScn to pupil splitting mirror SM, which folds the collection beam toward camera Cmr. At the pupil splitting mirror SM, the reflected light (or emitted light in the case of fluorescence imaging) is separated from the illumination light onto the detection path directed towards camera Cmr, which may be a digital camera having a photo sensor to capture an image. An imaging (e.g., objective) lens ImgL may be positioned in the detection path to image the fundus to the camera Cmr. As is the case for objective lens ObjL, imaging lens ImgL may be any type of lens known in the art (e.g., refractive, diffractive, reflective or hybrid lens). Additional operational details, in particular, ways to reduce artifacts in images, are described in PCT Publication No. WO2016/124644, the contents of which are herein incorporated in their entirety by reference. The camera Cmr captures the received image, e.g., it creates an image file, which can be further processed by one or more (electronic) processors or computing devices (e.g., the computer system of FIG. 16). Thus, the collection beam (returning from all scan positions of the scanning line beam SB) is collected by the camera Cmr, and a full-frame image Img may be constructed from a composite of the individually captured collection beams, such as by montaging. However, other scanning configuration are also contemplated, including ones where the illumination beam is scanned across the eye E and the collection beam is scanned across a photo sensor array of the camera. PCT Publication WO 2012/059236 and US Patent Publication No. 2015/0131050, herein incorporated by reference, describe several embodiments of slit scanning ophthalmoscopes including various designs where the returning light is swept across the camera's photo sensor array and where the returning light is not swept across the camera's photo sensor array.

In the present example, the camera Cmr is connected to a processor (e.g., processing module) Proc and a display (e.g., displaying module, computer screen, electronic screen, etc.) Dspl, both of which can be part of the image system itself, or may be part of separate, dedicated processing and/or displaying unit(s), such as a computer system wherein data is passed from the camera Cmr to the computer system over a cable or computer network including wireless networks. The display and processor can be an all in one unit. The display can be a traditional electronic display/screen or of the touch screen type and can include a user interface for displaying information to and receiving information from an instrument operator, or user. The user can interact with the display using any type of user input device as known in the art including, but not limited to, mouse, knobs, buttons, pointer, and touch screen.

It may be desirable for a patient's gaze to remain fixed while imaging is carried out. One way to achieve this is to provide a fixation target that the patient can be directed to stare at. Fixation targets can be internal or external to the instrument depending on what area of the eye is to be imaged. One embodiment of an internal fixation target is shown in FIG. 13. In addition to the primary light source LtSrc used for imaging, a second optional light source FxLtSrc, such as one or more LEDs, can be positioned such that a light pattern is imaged to the retina using lens FxL, scanning element FxScn and reflector/mirror FxM. Fixation scanner FxScn can move the position of the light pattern and reflector FxM directs the light pattern from fixation scanner FxScn to the fundus F of eye E. Preferably, fixation scanner FxScn is position such that it is located at the pupil plane of the system so that the light pattern on the retina/fundus can be moved depending on the desired fixation location.

Slit-scanning ophthalmoscope systems are capable of operating in different imaging modes depending on the light source and wavelength selective filtering elements employed. True color reflectance imaging (imaging similar to that observed by the clinician when examining the eye using a hand-held or slit lamp ophthalmoscope) can be achieved when imaging the eye with a sequence of colored LEDs (red, blue, and green). Images of each color can be built up in steps with each LED turned on at each scanning position or each color image can be taken in its entirety separately. The three, color images can be combined to display the true color image, or they can be displayed individually to highlight different features of the retina. The red channel best highlights the choroid, the green channel highlights the retina, and the blue channel highlights the anterior retinal layers. Additionally, light at specific frequencies (e.g., individual colored LEDs or lasers) can be used to excite different fluorophores in the eye (e.g., autofluorescence) and the resulting fluorescence can be detected by filtering out the excitation wavelength.

The fundus imaging system can also provide an infrared reflectance image, such as by using an infrared laser (or other infrared light source). The infrared (IR) mode is advantageous in that the eye is not sensitive to the IR wavelengths. This may permit a user to continuously take images without disturbing the eye (e.g., in a preview/alignment mode) to aid the user during alignment of the instrument. Also, the IR wavelengths have increased penetration through tissue and may provide improved visualization of choroidal structures. In addition, fluorescein angiography (FA) and indocyanine green (ICG) angiography imaging can be accomplished by collecting images after a fluorescent dye has been injected into the subject's bloodstream. For example, in FA (and/or ICG) a series of time-lapse images may be captured after injecting a light-reactive dye (e.g., fluorescent dye) into a subject's bloodstream. It is noted that care must be taken since the fluorescent dye may lead to a life-threatening allergic reaction in a portion of the population. High contrast, greyscale images are captured using specific light frequencies selected to excite the dye. As the dye flows through the eye, various portions of the eye are made to glow brightly (e.g., fluoresce), making it possible to discern the progress of the dye, and hence the blood flow, through the eye.

Optical Coherence Tomography Imaging System

In addition to fundus photography, fundus auto-fluorescence (FAF), fluorescein angiography (FA), ophthalmic images may also be created by other imaging modalities, such as, optical coherence tomography (OCT), OCT angiography (OCTA), and/or ocular ultrasonography. The present invention, or at least portions of the present invention with minor modification(s) as it would be understood in the art, may be applied to these other ophthalmic imaging modalities. More specifically, the present invention may also be applied to ophthalmic images produces by an OCT/OCTA system producing OCT and/or OCTA images. For instance, the present invention may be applied to en face OCT/OCTA images. Examples of fundus imagers are provided in U.S. Pat. Nos. 8,967,806 and 8,998,411, examples of OCT systems are provided in U.S. Pat. Nos. 6,741,359 and 9,706,915, and examples of an OCTA imaging system may be found in U.S. Pat. Nos. 9,700,206 and 9,759,544, all of which are herein incorporated in their entirety by reference. For the sake of completeness, an exemplary OCT/OCTA system is provided herein.

Figure 14:
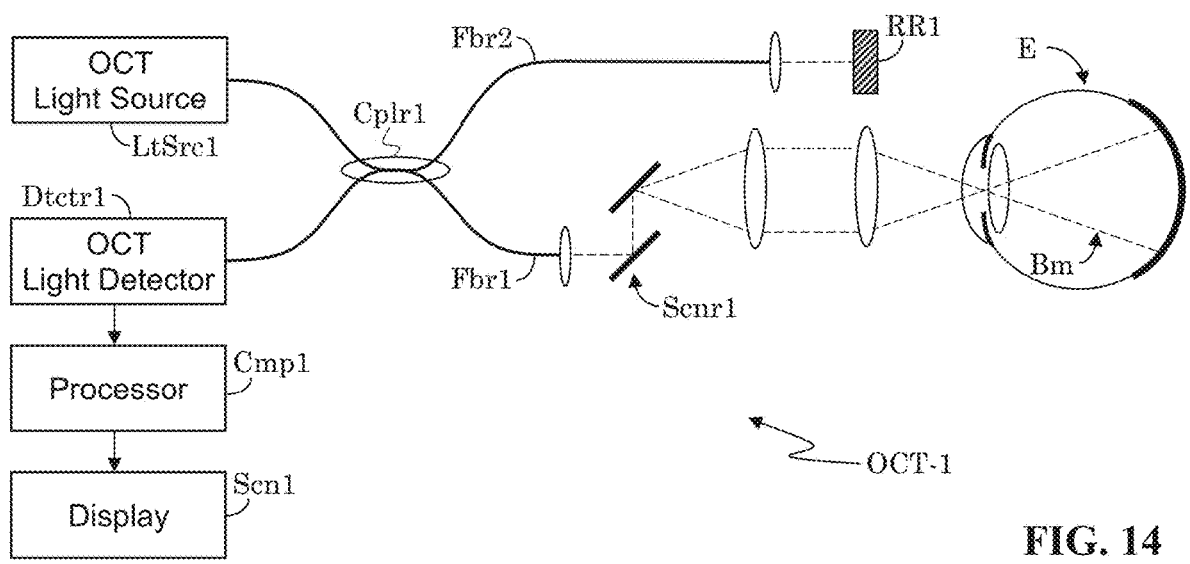
FIG. 14 illustrates a generalized frequency domain optical coherence tomography system used to collect 3-D image data of the eye suitable for use with the present invention.

FIG. 14 illustrates a generalized frequency domain optical coherence tomography (FD-OCT) system used to collect 3-D image data of the eye suitable for use with the present invention. An FD-OCT system OCT_1 includes a light source, LtSrc1. Typical light sources include, but are not limited to, broadband light sources with short temporal coherence lengths or swept laser sources. A beam of light from light source LtSrc1 is routed, typically by optical fiber Fbr1, to illuminate a sample, e.g., eye E; a typical sample being tissues in the human eye. The light source LrSrc1 can be either a broadband light source with short temporal coherence length in the case of spectral domain OCT (SD-OCT) or a wavelength tunable laser source in the case of swept source OCT (SS-OCT). The light may be scanned, typically with a scanner Scnr1 between the output of the optical fiber Fbr1 and the sample E, so that the beam of light (dashed line Bm) is scanned laterally (in x and y) over the region of the sample to be imaged. In the case of a full-field OCT, no scanner is needed and the light is applied across the entire, desired field of view (FOV) at once. Light scattered from the sample is collected, typically into the same optical fiber Fbr1 used to route the light for illumination. Reference light derived from the same light source LtSrc1 travels a separate path, in this case involving optical fiber Fbr2 and retro-reflector RR1 with an adjustable optical delay. Those skilled in the art will recognize that a transmissive reference path can also be used and that the adjustable delay could be placed in the sample or reference arm of the interferometer. Collected sample light is combined with reference light, typically in a fiber coupler Cplr1, to form light interference in an OCT light detector Dtctr1 (e.g., photodetector array, digital camera, etc.). Although a single fiber port is shown going to the detector Dtctr1, those skilled in the art will recognize that various designs of interferometers can be used for balanced or unbalanced detection of the interference signal. The output from the detector Dtctr1 is supplied to a processor Cmp1 (e.g., computing device) that converts the observed interference into depth information of the sample. The depth information may be stored in a memory associated with the processor Cmp1 and/or displayed on a display (e.g., computer/electronic display/screen) Scn1. The processing and storing functions may be localized within the OCT instrument or functions may be performed on an external processing unit (e.g., the computer system shown in FIG. 16) to which the collected data is transferred. This unit could be dedicated to data processing or perform other tasks which are quite general and not dedicated to the OCT device. The processor Cmp1 may contain, for example, a field-programmable gate array (FPGA), a digital signal processor (DSP), an application specific integrated circuit (ASIC), a graphics processing unit (GPU), a system on chip (SoC), a central processing unit (CPU), a general purpose graphics processing unit (GPGPU), or a combination thereof, that performs some, or the entire data processing steps, prior to passing on to the host processor or in a parallelized fashion.

The sample and reference arms in the interferometer could consist of bulk-optics, fiber-optics, or hybrid bulk-optic systems and could have different architectures such as Michelson, Mach-Zehnder or common-path based designs as would be known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—Holographic Optical Coherence Tomography," Optics Letters, 36(13): 2390 2011; Y. Nakamura, et al, "High-Speed Three Dimensional Human Retinal Imaging by Line Field Spectral Domain Optical Coherence Tomography," Optics Express, 15(12):7103 2007; Blazkiewicz et al, "Signal-To-Noise Ratio Study of Full-Field Fourier-Domain Optical Coherence Tomography," Applied Optics, 44(36):7722 (2005)). In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system. Various aspects of the invention could apply to any type of OCT system or other types of ophthalmic diagnostic systems and/or multiple ophthalmic diagnostic systems including but not limited to fundus imaging systems, visual field test devices, and scanning laser polarimeters.

In Fourier Domain optical coherence tomography (FD-OCT), each measurement is the real-valued spectral interferogram (Sj(k)). The real-valued spectral data typically goes through several post-processing steps including background subtraction, dispersion correction, etc. The Fourier transform of the processed interferogram, results in a complex valued OCT signal output $Aj(z)=|Aj|ei\varphi$. The absolute value of this complex OCT signal, $|Aj|$, reveals the profile of scattering intensities at different path lengths, and therefore scattering as a function of depth (z-direction) in the sample. Similarly, the phase, $\varphi j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. The term "cluster scan" may refer to a single unit or block of data generated by repeated acquisitions at the same (or substantially the same) location (or region) for the purposes of analyzing motion contrast, which may be used to identify blood flow. A cluster scan can consist of multiple A-scans or B-scans collected with relatively short time separations at approximately the same location(s) on the sample. Since the scans in a cluster scan are of the same region, static structures remain relatively unchanged from scan to scan within the cluster scan, whereas motion contrast between the scans that meets predefined criteria may be identified as blood flow. A variety of ways to create B-scans are known in the art including but not limited to: along the horizontal or x-direction, along the vertical or y-direction, along the diagonal of x and y, or in a circular or spiral pattern. B-scans may be in the x-z dimensions but may be any cross-sectional image that includes the z-dimension.

In OCT Angiography, or Functional OCT, analysis algorithms may be applied to OCT data collected at the same, or approximately the same, sample locations on a sample at different times (e.g., a cluster scan) to analyze motion or flow (see for example US Patent Publication Nos. 2005/0171438, 2012/0307014, 2010/0027857, 2012/0277579 and U.S. Pat. No. 6,549,801, all of which are herein incorporated in their entirety by reference). An OCT system may use any one of a number of OCT angiography processing algorithms (e.g., motion contrast algorithms) to identify blood flow. For example, motion contrast algorithms can be applied to the intensity information derived from the image data (intensity-based algorithm), the phase information from the image data (phase-based algorithm), or the complex image data (complex-based algorithm). An en face image is a 2D projection of 3D OCT data (e.g., by averaging the intensity of each individual A-scan, such that each A-scan defines a pixel in the 2D projection). Similarly, an en face vasculature image is an image displaying motion contrast signal in which the data dimension corresponding to depth (e.g., z-direction along an A-scan) is displayed as a single representative value (e.g., a pixel in a 2D projection image), typically by summing or integrating all or an isolated portion of the data (see for example U.S. Pat. No. 7,301,644 herein incorporated in its entirety by reference). OCT systems that provide an angiography imaging functionality may be termed OCT angiography (OCTA) systems.

Figure 15:
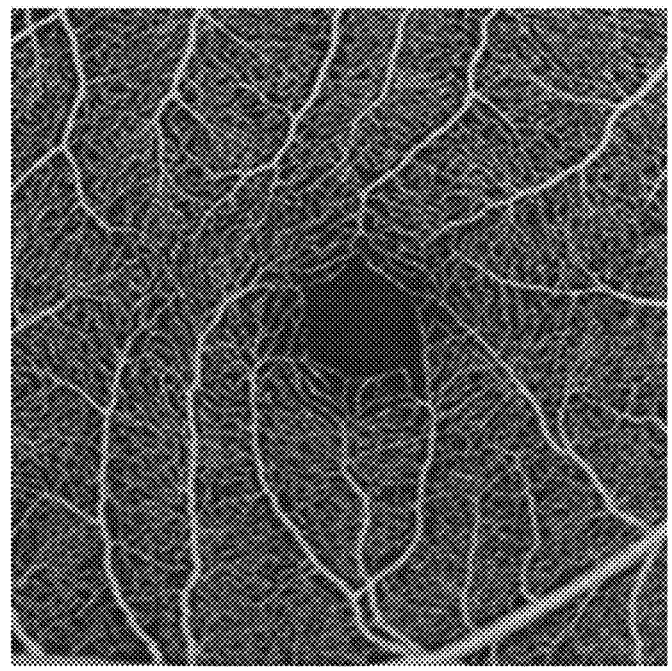
FIG. 15 shows an example of an en face vasculature image.

FIG. 15 shows an example of an en face vasculature image. After processing the data to highlight motion contrast using any of the motion contrast techniques known in the art, a range of pixels corresponding to a given tissue depth from the surface of internal limiting membrane (ILM) in retina, may be summed to generate the en face (e.g., frontal view) image of the vasculature.

Computing Device/System

Figure 16:
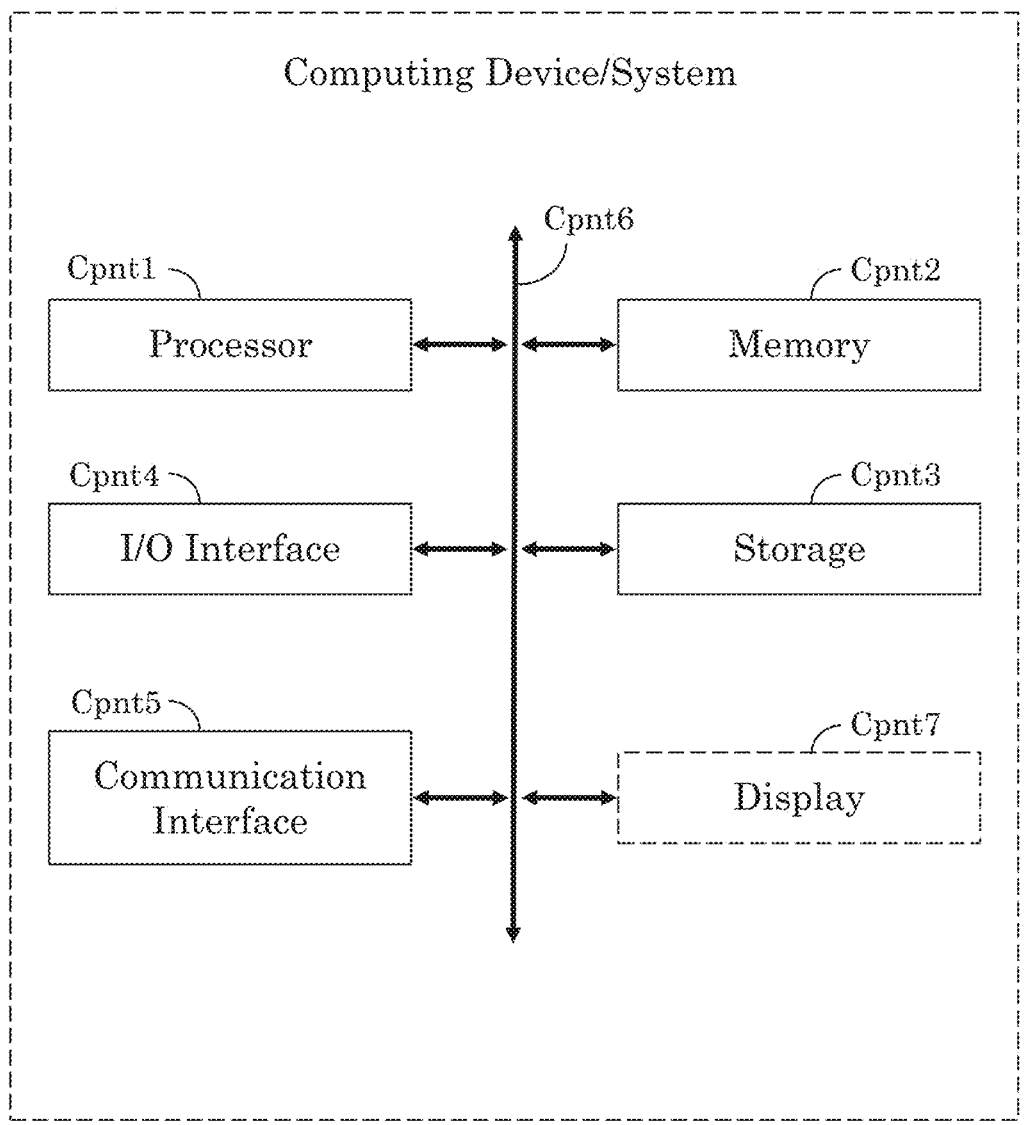
FIG. 16 illustrates an exemplary (stationary/portable/hand-held) computer system (or computing device or computer) suitable for use with the present invention.

FIG. 16 illustrates an example computer system (or computing device or computer device). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cpnt1, memory Cpnt2, storage Cpnt3, an input/output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In particular embodiments, processor Cpnt1 may include one or more internal caches for data, instructions, or addresses. Processor Cpnt1 may include one or more instruction caches, one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number of internal registers, and may include one or more arithmetic logic units (ALUs). Processor Cpnt1 may be a multi-core processor; or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or from another source (such as another computer system) to memory Cpnt2. Processor Cpnt1 may load the instructions and data from memory Cpnt2 to one or more internal register or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2 or storage Cpnt3. Bus Cpnt6 may include one or more memory buses (which may each include an address bus and a data bus) and may couple processor Cpnt1 to memory Cpnt2 and/or storage Cpnt3. Optionally, one or more memory management unit (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to the computer system, and include one or more of a disk drive (e.g., hard-disk drive, HDD, or solid-state drive, SSD), flash memory, ROM, EPROM, optical disc, magneto-optical disc, magnetic tape, Universal Serial Bus (USB)-accessible drive, or other type of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these.

Communication interface Cpnt5 may provide network interfaces for communication with other systems or networks. Communication interface Cpnt5 may include a Bluetooth interface or other type of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cpnt6 may provide a communication link between the above-mentioned components of the computing system. For example, bus Cpnt6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

The invention claimed is:

1. An ophthalmic system comprising:
a patient interface, including a face mask having a nasal bone frame configured to hold a patient's nose at a predefined position relative to the ophthalmic system that establishes a predefined alignment between an aperture of the ophthalmic system and an eye of the patient based on a personalized three-dimensional (3D) face model of the patient that defines a relative position of the patient's eye to the patient's nose.

2. The system of claim 1, wherein the ophthalmic system is one of an ophthalmic diagnostic system, ophthalmic treatment, or an ophthalmic medication dispensing system.

3. The system of claim 1, wherein the face mask is custom formed based on the 3D face model to custom fit the patient's face.

4. The system of claim 1, wherein the face mask has a preconfigured shape based on known contours of the patient's face as determined from the 3D face model and configured to provide a sensation-based feedback system for the patient indicating that the patient's face is in the predefined position that establishes the predefined alignment when a number of pressure points produced by the face mask is minimized.

5. The system of claim 1, wherein the face mask is at least partially 3D printed.

6. The system of claim 1, wherein the 3D face model is acquired by use of a 3D imaging device that implements one or more of laser triangulation 3D scanning technology, structured light 3D scanning technology, contact-based 3D scanning technology, time-of-flight 3D scanning technology, photogrammetry, a depth-sensing camera, and a multi-camera imaging system.

7. The system of claim 6, wherein the 3D imaging device is integral to a smart phone.

8. The system of claim 1, wherein the face mask is removable and replaceable in accordance with a patient's identification.

9. The system of claim 1, wherein the 3D face model is acquired by use of a mechanical scanning system, including an array of contact probes;
wherein the array of contact probes are displaced in response to the patient pressing their face into the mechanical scanning system, and the displaced positions of the contact probes define a height map stored in electronic memory.

10. The system of claim 1, wherein the face mask is embodied within a mechanical system including a plurality of contact probes, a displacement of the contact probes defining the contours of the face mask;
wherein the contact probes are moveable to target positions that define the contours of the face mask based on the 3D face model.

11. The system of claim 10, wherein:
the face mask includes an array of said contact probes covered by a flexible material that defines a surface of the face mask; and
the target positions of the contact probes are lockable in their displaced positions.

12. An ophthalmic system comprising:
a patient interface, including a face mask that establishes a predefined alignment between the ophthalmic system and an eye of the patient;
wherein:
the face mask is embodied within a mechanical scanning system including a plurality of contact probes, a displacement of the contact probes defining the contours of the face mask;
the contact probes are displaced in response to a patient pressing their face into the mechanical scanning system, and the displaced positions of the contact probes are lockable in their displaced positions; and
the displaced positions of the contact probes define a probe height map that is stored in electronic memory, and select contact probes are moveable to target positions specified by their corresponding, previously stored, probe height map.

13. The system of claim 12, wherein the electronic memory stores a plurality of probe height maps of different patients, and the face mask is configurable to any select patient, selected from among said plurality of different patients, by moving the select contact probes to their corresponding target positions according to the select patient's stored probe height map.

14. The system of claim 1, wherein:
the system includes an ophthalmic device and a connector coupling the face mask to the ophthalmic device; and
the connector is adapted to receive different types of ophthalmic devices.

15. The system of claim 14, wherein the different types of ophthalmic devices include one or more of a tonometer, medication dispenser, fundus imaging system, optical coherence tomography system, optical coherence tomography angiography system, biometry system, refractor, visual field tester, surgical apparatus, ophthalmic laser, and wavefront sensor.

16. The system of claim 1, wherein:
the system includes an ophthalmic device and a connector coupling the face mask to the ophthalmic device;
the face mask is one of multiple personalized face masks each personalized to a different patient; and
the connector is adapted to selectively receive any of the multiple personalized face masks.

17. The system of claim 1, wherein the face mask is one of a full face or a partial face mask not encircling the patient's eye socket.

18. The system of claim 1, wherein the face mask is a partial face mask configured to align only to boney sections of the patient's face, including the nasal bone.

19. The system of claim 1, wherein the face mask is a partial face mask integrated to a patient interface, and a portion of the patient's face not covered by the face mask is fitted to the patient interface.

20. The system of claim 1, wherein the ophthalmic system is portable.

21. The system of claim 1, wherein the ophthalmic system includes a fixation target.

22. The system of claim 1, wherein the ophthalmic system includes one or more of a fundus imaging system, an optical coherence tomography system, optical coherence tomography angiography system, a biometry system, refractor, visual field tester, wavefront sensor, tonometer, surgical apparatus, ophthalmic laser, and medication dispenser.

23. The system of claim 1, wherein the face mask includes a light shield that forms a light proof enclosure shielding the eye from ambient light, and enabling natural dilation of the eye by blocking the ambient light from the eye.

24. The system of claim 1, wherein the face mask enables natural dilation of the eye by blocking ambient light from the eye.

25. The system of claim 1 wherein:
the system includes an ophthalmic device;
the interior configuration of the face mask is specific to the patient; and
the exterior configuration of the face mask is specific to the device.

26. The system of claim 1, wherein:
the predefined alignment between an aperture of the ophthalmic system and an eye of the patient is established within one tenth of a millimeter in 3D space.

27. The system of claim 1, wherein:
the aperture of the ophthalmic system is divided into an illumination part defining a region through which light that enters the eye passes and a collection part through which light that exits the eye is collected for imaging; and
and the eye is aligned to these parts of the aperture.

28. The system of claim 1, wherein the predefined position is a single position with a predefined orientation relative to the ophthalmic system.

29. The system of claim 1, wherein:
the ophthalmic system accommodates a plurality of said patients;
each patient has a respective, associated the 3D face model based on the patient's identification; and
at least the nasal bone frame of the face mask is reconfigurable based on a patient's associated 3D face model as determined from the patient's identification.

* * * * *